US012742140B2

(12) United States Patent
Tanabe et al.

(10) Patent No.: US 12,742,140 B2
(45) Date of Patent: Sep. 22, 2026

(54) CULTURING SYSTEM AND METHOD FOR CULTURING CELLS

(71) Applicants: I Peace, Inc., Palo Alto, CA (US); Koji Tanabe, Palo Alto, CA (US)

(72) Inventors: Koji Tanabe, Palo Alto, CA (US); Kenta Suto, Kyoto (JP); Ryoji Hiraide, Kyoto (JP)

(73) Assignees: I Peace, Inc., Palo Alto, CA (US); Koji Tanabe, Palo Alto, CA (US)

( * ) Notice: Subject to any disclaimer, the term of this patent is extended or adjusted under 35 U.S.C. 154(b) by 855 days.

(21) Appl. No.: 18/157,369

(22) Filed: Jan. 20, 2023

(65) Prior Publication Data

US 2023/0313102 A1 Oct. 5, 2023

(30) Foreign Application Priority Data

Jan. 24, 2022 (JP) ................................ 2022-008525

(51) Int. Cl.
*C12M 1/00* (2006.01)

(52) U.S. Cl.
CPC ............ *C12M 23/58* (2013.01); *C12M 29/00* (2013.01)

(58) Field of Classification Search
None
See application file for complete search history.

(56) References Cited

U.S. PATENT DOCUMENTS

2015/0072401 A1 3/2015 Nozaki et al.
2016/0326476 A1* 11/2016 Maisch .................. C12M 23/40
2021/0024875 A1* 1/2021 Magness ............ B01D 19/0063
2021/0269760 A1* 9/2021 Farmer .................... C12N 1/14

FOREIGN PATENT DOCUMENTS

JP 2016-208866 A 12/2016
WO 2013/145235 A1 10/2013

* cited by examiner

*Primary Examiner* — Holly Kipouros
(74) *Attorney, Agent, or Firm* — Studebaker Brackett PLLC

(57) ABSTRACT

The present invention provides a culturing system and method for culturing cells that can culture cells in parallel. The culturing system comprises a cell storage 10 configured to store cells, a plurality of culture apparatuses 20, and a distribution flow path 30 configured to distribute the cells from the cell storage 10 to the culture apparatuses 20, in which each of the culture apparatuses 20 comprises a plurality of culture vessels 21, a supply flow path 22 configured to selectively supply a fluid from the distribution flow path 30 to the culture vessels 21, and a connection flow path 23 configured to connect the culture vessels 21; the culture vessels 21 are connected in series with the connection flow path 23 in each of the culture apparatuses 20; and the supply flow path 22 is configured to selectively supply the fluid to the culture vessels so that the cells are sequentially transferred among the culture vessels 21 through the connection flow path 23 in each of the culture apparatuses 20.

9 Claims, 5 Drawing Sheets

10
11A
11B
11C
11D
33
32
34A
34B
34C
34D
30
31
20A
20B
20C
21AA
21AB
21AC
21BA
21BB
21BC
21CA
21CB
21CC
22A
22B
22C
23A
23B
23C
24AA
24AB
24AC
24BA
24BB
24BC
24CA
24CB
24CC
25AA
25AB
25BA
25BB
25CA
25CB
26A
26B
26C
27AA
27AB
27AC
27BA
27BB
27BC
27CA
27CB
27CC
28A
28B
28C
40A
40B
40C
41A
41B
41C
50
301

10
11A
11B
11C
11D
33
34A
34B
34C
34D
32
30
31
20A
20B
20C
21AA
21AB
21AC
21BA
21BB
21BC
21CA
21CB
21CC
22A
22B
22C
23A
23B
23C
24AA
24AB
24AC
24BA
24BB
24BC
24CA
24CB
24CC
25AA
25AB
25BA
25BB
25CA
25CB
26A
26B
26C
27AA
27AB
27AC
27BA
27BB
27BC
27CA
27CB
27CC
28A
28B
28C
40A
40B
40C
41A
41B
41C
50
60AA
60AB
60BA
60BB
60CA
60CB
301

10
11A
11B
11C
11D
11E
33
32
34A
34B
34C
34D
34E
30
31
20A
20B
20C
21AA
21AB
21AC
21BA
21BB
21BC
21CA
21CB
21CC
22A
22B
22C
23A
23B
23C
24AA
24AB
24AC
24BA
24BB
24BC
24CA
24CB
24CC
25AA
25AB
25BA
25BB
25CA
25CB
26A
26B
26C
27AA
27AB
27AC
27BA
27BB
27BC
27CA
27CB
27CC
28A
28B
28C
40A
40B
40C
41A
41B
41C
50
301

10A
10B
10C
11A
11B
11C
11D
11E
33A
33B
33C
34A
34B
34C
34D
34E
30
32
31
30
30
30
21AA
20A
22A
23A
26A
24AA
27AA
25AA
22A
21AB
24AB
23A
26A
27AB
22A
25AB
24AC
21AC
26A
27AC
28A
40A
41A
20B
22B
21BA
26B
27BA
24BA
23B
25BA
22B
21BB
24BB
26B
27BB
25BB
22B
21BC
26B
24BC
27BC
28B
40B
41B
20C
22C
21CA
26C
27CA
24CA
23C
25CA
22C
21CB
27CB
24CB
26C
23C
25CB
22C
26C
27CC
24CC
21CC
28C
40C
41C
50
301

CULTURING SYSTEM AND METHOD FOR CULTURING CELLS

BACKGROUND

Field

The present invention relates to a culturing system and a method for culturing cells.

Description of Related Art

Systems for automatically culturing cells have been proposed (e.g., see Patent Literatures 1 and 2).

CITATION LIST

Patent Literatures

[Patent Literature 1] WO 2013/145235
[Patent Literature 2] Japanese Patent Laid-Open No. 2016-208866

SUMMARY

Technical Problem

The present invention aims to provide a culturing system and a method for culturing cells that can culture cells in parallel.

Solution to Problem

A culturing system according to an aspect of the present invention comprises a cell storage configured to store cells, a plurality of culture apparatuses, and a distribution flow path configured to distribute the cells from the cell storage to the culture apparatuses, in which each of the culture apparatuses comprises a plurality of culture vessels, a supply flow path configured to selectively supply a fluid from the distribution flow path to the culture vessels, and a connection flow path configured to connect the culture vessels; the culture vessels are connected in series with the connection flow path in each of the culture apparatuses; and the supply flow path is configured to selectively supply a fluid to the culture vessels so that the cells are sequentially transferred among the culture vessels through the connection flow path in each of the culture apparatuses.

The culturing system may further comprise a fluid machinery configured to supply a fluid from the distribution flow path to the supply flow path in each of the culture apparatuses.

In the culturing system, each of the culture apparatuses may further comprise a plurality of supply valves provided in the supply flow path.

In the culturing system, the supply valves may correspond to the culture vessels, respectively in each of the culture apparatuses.

In the culturing system, each of the culture apparatuses may further comprise a connection valve provided in the connection flow path.

In the culturing system, the connection valve may be provided between the culture vessels.

In the culturing system, each of the culture apparatuses may further comprise an intermediate tank provided in the connection flow path.

In the culturing system, the intermediate tank may be provided between the culture vessels.

In the culturing system, each of the culture apparatuses may further comprise a discharge flow path configured to selectively discharge a fluid from the culture vessels.

In the culturing system, each of the culture apparatuses may further comprise a plurality of discharge valves provided in the discharge flow path.

In the culturing system, the discharge valves may correspond to the culture vessels, respectively, in each of the culture apparatuses.

In the culturing system, the discharge flow path may be configured to selectively discharge a fluid from the culture vessels so that the cells are sequentially transferred among the culture vessels through the connection flow path in each of the culture apparatuses.

In the culturing system, each of the culture apparatuses further comprises a plurality of supply valves provided in the supply flow path, a discharge flow path configured to selectively discharge a fluid from the culture vessels, and a plurality of discharge valves provided in the discharge flow path, in which the supply valves may correspond to the culture vessels, respectively, in each of the culture apparatuses; the discharge valves may correspond to the culture vessels, respectively, in each of the culture apparatuses; one of the supply valves corresponding to one of the culture vessels that is to be provided with the cells from the cell storage may be opened; and one of the discharge valves corresponding to one of the culture vessels that is to be provided with the cells from the cell storage may be opened.

In the culturing system, each of the culture apparatuses further comprises a plurality of supply valves provided in the supply flow path, a discharge flow path configured to selectively discharge a fluid from the culture vessels, and a plurality of discharge valves provided in the discharge flow path, in which the supply valves may correspond to the culture vessels, respectively, in each of the culture apparatuses; the discharge valves may correspond to the culture vessels, respectively, in each of the culture apparatuses; one of the supply valves corresponding to one of the culture vessels that is to be provided with the fluid may be opened; and one of the discharge valves corresponding to one of the culture vessels that is to be provided with the fluid may be opened.

In the culturing system, each of the culture apparatuses further comprises a plurality of supply valves provided in the supply flow path, a plurality of connection valves provided in the connection flow paths, a discharge flow path configured to selectively discharge a fluid from the culture vessels, and a plurality of discharge valves provided in the discharge flow path, in which the supply valves may correspond to the culture vessels, respectively, in each of the culture apparatuses; the connection valve may be provided between the culture vessels in each of the culture apparatuses; the discharge valves may correspond to the culture vessels, respectively, in each of the culture apparatuses; one of the supply valves corresponding to one of the culture vessels where the cells are disposed may be opened; the connection valve between the culture vessel where the cells are disposed and a culture vessel adjacent to the culture vessel where the cells are disposed may be opened; and one of the discharge valves corresponding to the adjacent culture vessel may be opened.

In the culturing system, one of the discharge valves corresponding to the culture vessel where the cells are disposed may be closed, and one of the supply valves corresponding to the adjacent culture vessel may be closed.

The culturing system may further comprise one or more fluid storages configured to store a fluid, and the distribution flow path may be configured to distribute the fluid from the fluid storages to the culture apparatuses.

In the culturing system, the fluid may comprise a medium, a buffer, a cell detachment agent, a cryopreservation agent, or a factor.

A method for culturing cells according to an aspect of the present invention comprises preparing a culturing system that comprises a cell storage configured to store cells, a plurality of culture apparatuses, and a distribution flow path configured to distribute the cells from the cell storage to the culture apparatuses, in which each of the culture apparatuses comprises a plurality of culture vessels, a supply flow path configured to selectively supply a fluid from the distribution flow path to the culture vessels, and a connection flow path configured to connect the culture vessels; distributing the cells from the cell storage to each of the culture apparatuses through the distribution flow path; supplying the cells to at least one of the culture vessels through the supply flow path in each of the culture apparatuses; and culturing the cells in at least one of the culture vessels in each of the culture apparatuses.

In the method for culturing cells, each of the culture apparatuses may further comprise a discharge flow path configured to selectively discharge a fluid from the culture vessels, and in the supplying the cells to at least one of the culture vessels through the supply flow path in each of the culture apparatuses, the fluid in at least one of the culture vessels may be discharged to the discharge flow path.

The method for culturing cells may further comprise supplying the fluid to one of the culture vessels where the cells are disposed through the supply flow path in each of the culture apparatuses.

In the method for culturing cells, each of the culture apparatuses may further comprise a discharge flow path configured to selectively discharge a fluid from the culture vessels, and in the supplying the fluid to one of the culture vessels where the cells are disposed through the supply flow path in each of the culture apparatuses, the fluid in one of the culture vessels where the cells are disposed may be discharged to the discharge flow path.

The method for culturing cells may further comprise transferring the cells from the culture vessel where the cells are disposed to another culture vessel through the connection flow path in each of the culture apparatuses.

In the method for culturing cells, each of the culture apparatuses may further comprise a discharge flow path configured to selectively discharge a fluid from the culture vessels, and in the transferring the cells from the culture vessel where the cells are disposed to another culture vessel through the connection flow path in each of the culture apparatuses, a fluid in the other culture vessel may be discharged to the discharge flow path.

In the method for culturing cells, the fluid may be a gas, a liquid, or a gel.

In the method for culturing cells, the fluid may comprise a medium, a buffer, a cell detachment agent, a cryopreservation agent, or a factor.

In the method for culturing cells, the fluid may comprise a factor, and the cells may be induced into another state by the factor, in at least one of the culture vessels in each of the culture apparatuses.

Advantageous Effects of Invention

The present invention enables provision of a culturing system and a method for culturing cells that can culture cells in parallel.

DETAILED DESCRIPTION

Figure 1:
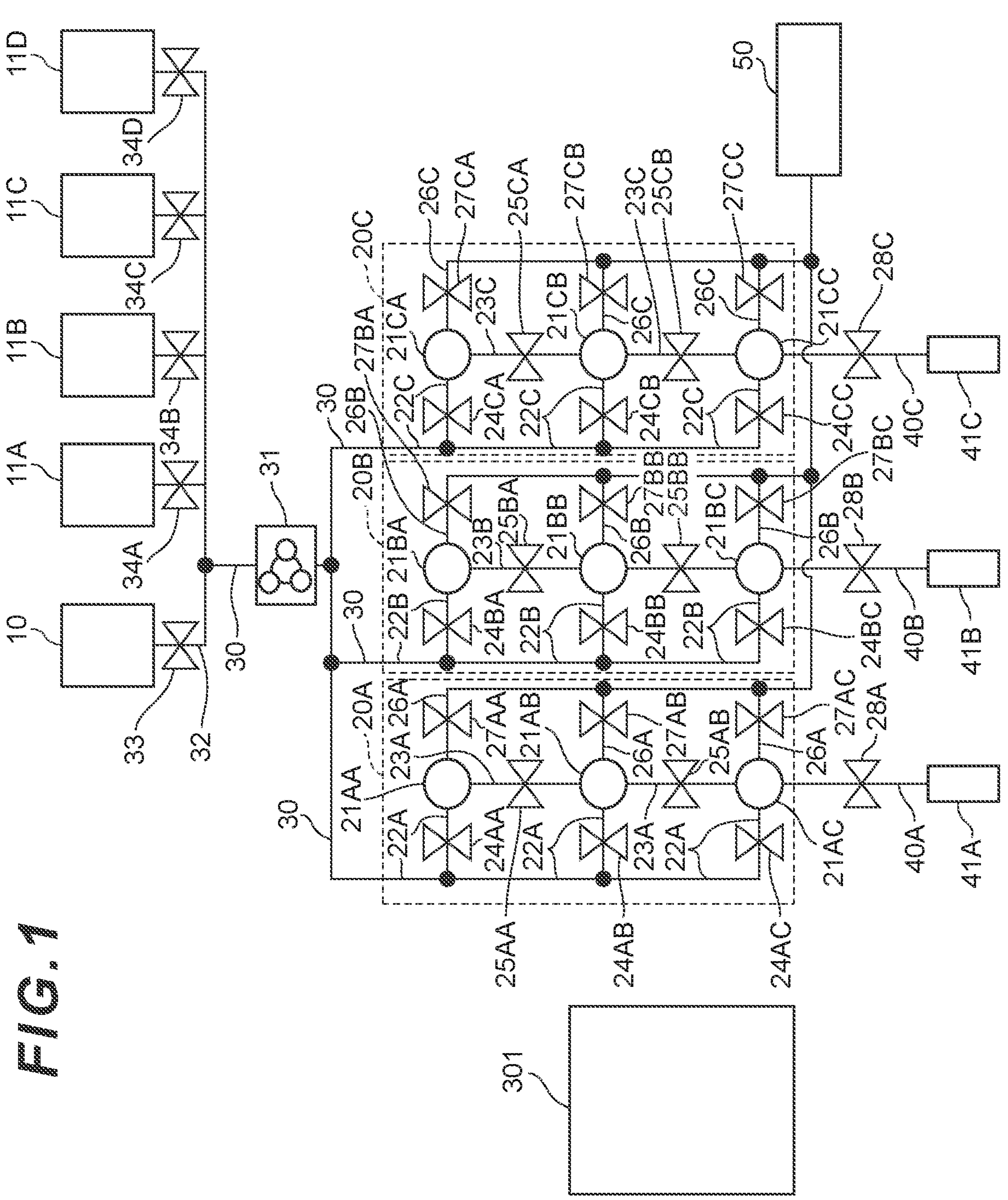
FIG. 1 is a schematic diagram of a culturing system according to the first embodiment.

Embodiments of the present invention will be described below. In the following description of the drawings, identical or similar portions are indicated by identical or similar symbols. It is noted that the drawings are schematic. Thus, specific dimensions and the like should be determined in the light of the following description. Naturally, the drawings may include portions shown with different dimensions or ratios from those shown in other drawings.

First Embodiment

A culturing system according to the first embodiment comprises a cell storage 10 configured to store cells, a plurality of culture apparatuses 20A, 20B, and 20C, and a distribution flow path 30 configured to distribute the cells from the cell storage 10 to the culture apparatuses 20A, 20B, and 20C. The number of the culture apparatuses 20A, 20B, and 20C is not limited to particular numbers.

Each of the culture apparatuses 20A, 20B, and 20C comprises a plurality of culture vessels 21, a supply flow path 22 configured to selectively supply a fluid from the distribution flow path 30 to the culture vessels 21, and a connection flow path 23 that connects the culture vessels 21. The number of the culture vessels 21 is not limited to particular numbers. The fluid includes a gas, a liquid, and a gel.

In each of the culture apparatuses 20A, 20B, and 20C, the culture vessels 21 are connected in series with the connection flow paths 23. In each of the culture apparatuses 20A, 20B, and 20C, the supply flow path 22 is configured to selectively supply the fluid to the culture vessels 21 so that the cells are sequentially transferred among the culture vessels 21 through the connection flow paths 23.

The culturing system may further comprise fluid storages 11A, 11B, 11C, and 11D. The number of the fluid storages 11A, 11B, 11C, and 11D is not limited to particular numbers. The cells stored in the cell storage 10 are not limited to particular cells. The fluids stored in the fluid storages 11A, 11B, 11C, and 11D are not limited to particular fluids. For example, the first fluid storage 11A stores a medium. The second fluid storage 11B stores a detachment agent. The third fluid storage 11C stores a cryopreservation agent. The fourth fluid storage 11D stores a gas. For example, the cell storage 10 and the fluid storages 11A, 11B, 11C, and 11D have a variable volume.

For example, the cell storage 10 and the fluid storages 11A, 11B, 11C, and 11D are connected to a confluence flow path 32. The cell storage 10 and the fluid storages 11A, 11B, 11C, and 11D may be aseptically connected to the confluence flow path 32. The confluence flow path 32 is connected to the distribution flow path 30. In the confluence flow path 32, a plurality of confluence valves 33, 34A, 34B, 34C, and 34D corresponding to the cell storage 10 and the fluid storages 11A, 11B, 11C, and 11D, respectively, are provided. When ambient air is used as a gas, the fluid storage 11D is not required to be connected to the confluence flow path 32. In this case, opening the confluence valve 34D allows ambient air to be taken in the confluence flow path 32. The opening in the confluence flow path 32 to take ambient air may have a filter.

When the cells are transferred from the cell storage 10 to the distribution flow path 30 through the confluence flow path 32, the confluence valve 33 corresponding to the cell storage 10 is opened, and the other confluence valves 34A, 34B, 34C, and 34D are closed.

When the medium is transferred from the first fluid storage 11A to the distribution flow path 30 through the confluence flow path 32, the confluence valve 34A corresponding to the first fluid storage 11A is opened, and the other confluence valves 33, 34B, 34C, and 34D are closed.

When the detachment agent is transferred from the second fluid storage 11B to the distribution flow path 30 through the confluence flow path 32, the confluence valve 34B corresponding to the second fluid storage 11B is opened, and the other confluence valves 33, 34A, 34C, and 34D are closed.

When the cryopreservation agent is transferred from the third fluid storage 11C to the distribution flow path 30 through the confluence flow path 32, the confluence valve 34C corresponding to the third fluid storage 11C is opened, and the other confluence valves 33, 34A, 34B, and 34D are closed.

When the gas is transferred from the fourth fluid storage 11D to the distribution flow path 30 through the confluence flow path 32, the confluence valve 34D corresponding to the fourth fluid storage 11D is opened, and the other confluence valves 33, 34A, 34B, and 34C are closed.

The distribution flow path 30 connects any of the cell storage 10 and the fluid storages 11A, 11B, 11C, and 11D to the culture apparatuses 20A, 20B, and 20C. The distribution flow path 30 branches to be connected to the culture apparatuses 20A, 20B, and 20C. The distribution flow path 30 may have a fluid machinery 31 that transfers the fluid in the distribution flow path 30. The fluid machinery 31 is, for example, a pump.

The cells in the cell storage 10 are distributed to the culture apparatuses 20A, 20B, and 20C by the fluid machinery 31 through the confluence flow path 32 and the distribution flow path 30. For example, the same type and amount of cells may be distributed to the culture apparatuses 20A, 20B, and 20C. Alternatively, the cells distributed to the culture apparatuses 20A, 20B, and 20C may be different in at least either type or amount.

The medium in the first fluid storage 11A is distributed to the culture apparatuses 20A, 20B, and 20C by the fluid machinery 31 through the confluence flow path 32 and the distribution flow path 30. For example, the same type and amount of medium may be distributed to the culture apparatuses 20A, 20B, and 20C. Alternatively, the medium distributed to the culture apparatuses 20A, 20B, and 20C may have different amounts.

The detachment agent in the second fluid storage 11B is distributed to the culture apparatuses 20A, 20B, and 20C by the fluid machinery 31 through the confluence flow path 32 and the distribution flow path 30. For example, the same type and amount of detachment agent may be distributed to the culture apparatuses 20A, 20B, and 20C. Alternatively, the detachment agent distributed to the culture apparatuses 20A, 20B, and 20C may have different amounts.

The cryopreservation agent in the third fluid storage 11C is distributed to the culture apparatuses 20A, 20B, and 20C by the fluid machinery 31 through the confluence flow path 32 and the distribution flow path 30. For example, the same type and amount of cryopreservation agent may be distributed to the culture apparatuses 20A, 20B, and 20C. Alternatively, the cryopreservation agent distributed to the culture apparatuses 20A, 20B, and 20C may have different amounts.

The gas in the fourth fluid storage 11D is distributed to the culture apparatuses 20A, 20B, and 20C by the fluid machinery 31 through the confluence flow path 32 and the distribution flow path 30. For example, the same type and amount of gas may be distributed to the culture apparatuses 20A, 20B, and 20C. Alternatively, the gas distributed to the culture apparatuses 20A, 20B, and 20C may have different amounts.

In each of the culture apparatuses 20A, 20B, and 20C, the distribution flow path 30 is connected to a supply flow path 22. The supply flow path 22 branches to be connected to a plurality of culture vessels 21. In the branched supply flow path 22, a plurality of supply valves 24 corresponding to the plurality of culture vessels 21, respectively, are provided. When a fluid is supplied to any one of the culture vessels 21, the supply valve 24 corresponding to the vessel is opened, and the other supply valves 24 are closed.

Each of the culture apparatuses 20A, 20B, and 20C may further comprise connection valves 25 provided in the connection flow path 23. For example, each of the connection valves 25 is placed between the adjacent culture vessels 21. When a fluid is transferred between any one pair of culture vessels 21, a connection valve 25 between the pair of culture vessels 21 is opened, and the other connection valves 25 are closed.

Figure 2:
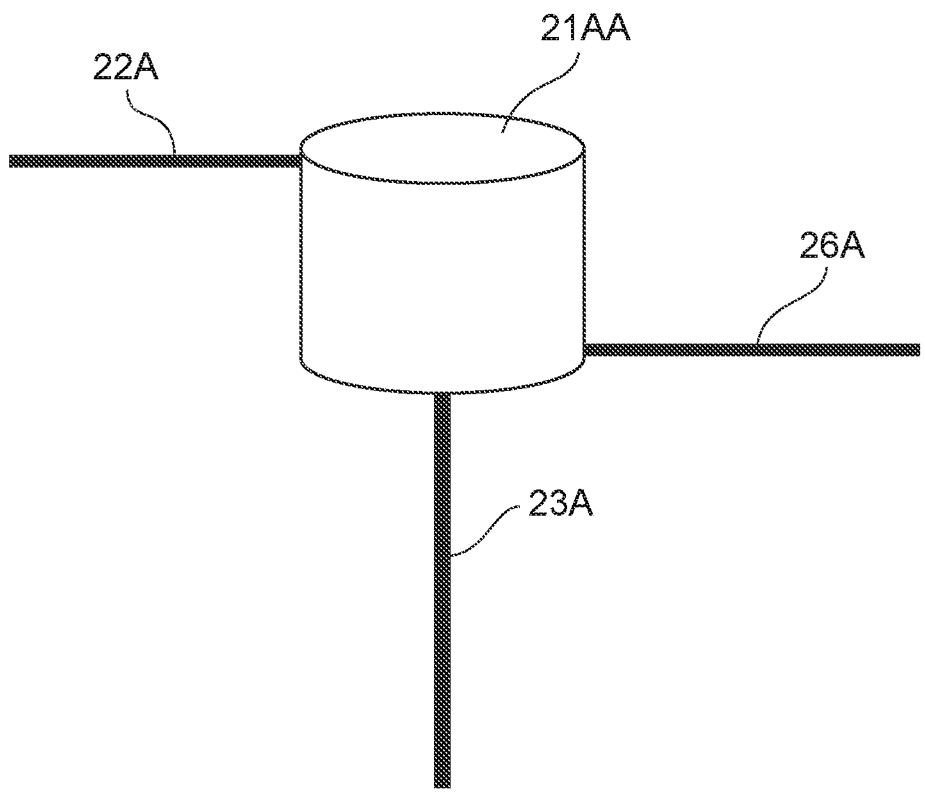
FIG. 2 is a schematic diagram of a culturing system according to the first embodiment.

Each of the culture apparatuses 20A, 20B, and 20C may further comprise a discharge flow path 26 configured to selectively discharge the fluid from a plurality of culture vessels 21. The discharge flow path 26 is connected to the culture vessels 21. In the discharge flow path 26, a plurality of discharge valves 27 corresponding to the culture vessels 21, respectively, are provided. When a fluid is discharged from any one of the culture vessels 21, the discharge valve 27 corresponding to the vessel is opened, and the other discharge valves 27 are closed. It should be noted that the supply flow path 22 may be connected to the culture vessel 21 at an upper position and to the discharge flow path 26 and the connection flow path 23 at lower positions when the direction of gravitational force is viewed downward, as shown in FIG. 2.

A cell harvesting vessel 41 may be connected through a cell harvesting flow path 40 to at least one of the culture vessels 21 in each of the culture apparatuses 20A, 20B, and 20C shown in FIG. 1. The cell harvesting flow path 40 may have a harvesting valve 28. The cell harvesting vessel 41 may be aseptically connected to the cell harvesting flow path 40. The discharge flow path 26 in each of the culture apparatuses 20A, 20B, and 20C may be connected to a discharge vessel 50. For example, the cell harvesting vessel 41 and the discharge vessel 50 have a variable volume.

The culturing system according to the first embodiment may further comprise a controller 301 that controls the fluid machinery 31, the confluence valves 33 and 34, the supply valve 24, the discharge valve 27, and the harvesting valve 28. The controller 301 controls, for example, a flow, a flow rate, and a fluid pressure of a fluid moved by the fluid machinery 31. The controller 301 controls, for example, opening or closing of the confluence valves 33 and 34, the supply valve 24, the discharge valve 27, and the harvesting valve 28 and a flow, a flow rate, and a fluid pressure of a fluid passing through the confluence valves 33 and 34, the supply valve 24, the discharge valve 27, and the harvesting valve 28.

Next, a method for culturing cells using the culturing system according to the first embodiment will be described.

The controller 301 opens the first supply valve 24AA and the first discharge valve 27AA corresponding to the first culture vessel 21AA in the first culture apparatus 20A and closes the other supply valves 24AB and 24AC, the other discharge valves 27AB and 27AC, the connection valves 25AA and 25AB, and the harvesting valve 28 in the first culture apparatus 20A.

The controller 301 opens the first supply valve 24BA and the first discharge valve 27BA corresponding to the first culture vessel 21BA in the second culture apparatus 20B and closes the other supply valves 24BB and 24BC, the other discharge valves 27BB and 27BC, the connection valves 25BA and 25BB, and the harvesting valve 28B in the second culture apparatus 20B.

The controller 301 opens the first supply valve 24CA and the first discharge valve 27CA corresponding to the first culture vessel 21CA in the third culture apparatus 20C and closes the other supply valves 24CB and 24CC, the other discharge valves 27CB and 27CC, the connection valves 25CA and 25CB, and the harvesting valve 28C in the third culture apparatus 20C.

The controller 301 opens the confluence valve 33 corresponding to the cell storage 10 and closes the other confluence valves 34A, 34B, 34C, and 34D. The controller 301 controls the fluid machinery 31 to move a fluid in the distribution flow path 30 toward the first to third culture apparatuses 20A, 20B, and 20C. This allows the movement of fluid comprising the cells in the cell storage 10 to the distribution flow path 30 through the confluence flow path 32. The fluid comprising the cells is, for example, a medium. Next, the controller 301 opens the confluence valve 34D corresponding to the fourth fluid storage 11D storing a gas and closes the other confluence valves 33, 34A, 34B, and 34C. This allows the movement of, following the fluid comprising the cells, the gas to the distribution flow path 30 through the confluence flow path 32. The fluid comprising the cells is distributed to the first to third culture apparatuses 20A, 20B, and 20C through the distribution flow path 30. Following the fluid comprising the cells, the gas is distributed to the first to third culture apparatuses 20A, 20B, and 20C through the distribution flow path 30.

The fluid comprising the cells moved from the distribution flow path 30 to the supply flow path 22A in the first culture apparatus 20A arrives at the first culture vessel 21AA. The fluid comprising the cells pushes a fluid in the first culture vessel 21AA, such as a gas, to move it to the discharge vessel 50 through the discharge flow path 26A.

The fluid comprising the cells moved from the distribution flow path 30 to the supply flow path 22B in the second culture apparatus 20B arrives at the first culture vessel 21BA. The fluid comprising the cells pushes a fluid in the first culture vessel 21BA, such as a gas, to move it to the discharge vessel 50 through the discharge flow path 26B.

The fluid comprising the cells moved from the distribution flow path 30 to the supply flow path 22C in the third culture apparatus 20C arrives at the first culture vessel 21CA. The fluid comprising the cells pushes a fluid in the first culture vessel 21CA, such as a gas, to move it to the discharge vessel 50 through the discharge flow path 26C.

The length of the distribution flow path 30 and/or the supply flow path 22 may be set so that the fluid comprising the cells arrives at the first culture vessels 21AA, 21BA, and 21CA in the first to third culture apparatuses 20A, 20B, and 20C at the same time. For example, the length of the distribution flow path 30 and/or the supply flow path 22 may be set so that the flow paths from the cell storage 10 to each of the first culture vessels 21AA, 21BA, and 21CA have the same length. It should be noted that the first supply valves 24AA, 24BA, and 24CA may be opened at different times to cause arrival of the fluid comprising cells at the first culture vessels 21AA, 21BA, and 21CA in the first to third culture apparatuses 20A, 20B, and 20C at different times.

Once the fluid comprising the cells has entered the first culture vessels 21AA, 21BA, and 21CA in the first to third culture apparatuses 20A, 20B, and 20C, the controller 301 controls the fluid machinery 31 to stop the movement of fluid. The controller 301 closes the first supply valve 24AA and the first discharge valve 27AA in the first culture apparatus 20A, the first supply valve 24BA and the first discharge valve 27BA in the second culture apparatus 20B, and the first supply valve 24CA and the first discharge valve 27CA in the third culture apparatus 20C. The cells are cultured in each of the first culture vessels 21AA, 21BA, and 21CA in the first to third culture apparatuses 20A, 20B, and 20C over a predetermined period. The culture may be adhesive culture or suspension culture. The culture may be two-dimensional culture or three-dimensional culture.

When the media in the first culture vessels 21AA, 21BA, and 21CA are replaced, the controller 301 opens the first supply valve 24AA and the first discharge valve 27AA in the first culture apparatus 20A and closes the other supply valves 24AB and 24AC and the other discharge valves 27AB and 27AC. The controller 301 opens the first supply valve 24BA and the first discharge valve 27BA in the second culture apparatus 20B and closes the other supply valves 24BB and 24BC and the other discharge valves 27BB and 27BC. The controller 301 opens the first supply valve 24CA and the first discharge valve 27CA in the third culture apparatus 20C and closes the other supply valves 24CB and 24CC and the other discharge valves 27CB and 27CC. The controller 301 also opens the confluence valve 34A, closes the other confluence valves 33, 34B, 34C, and 34D, controls the fluid machinery 31 to move the unused medium in the first fluid storage 11A toward the first to third culture apparatuses 20A, 20B, and 20C through the confluence flow path 32 and the distribution flow path 30.

The unused medium moved to the supply flow path 22A in the first culture apparatus 20A through the distribution flow path 30 arrives at the first culture vessel 21AA. The unused medium pushes used medium in the first culture vessel 21AA to move it to the discharge vessel 50 through the discharge flow path 26A. This allows the replacement of medium in the first culture vessel 21AA.

The unused medium moved from the distribution flow path 30 to the supply flow path 22B in the second culture apparatus 20B arrives at the first culture vessel 21BA. The unused medium pushes used medium in the first culture vessel 21BA to move it to the discharge vessel 50 through the discharge flow path 26B. This allows the replacement of medium in the first culture vessel 21BA.

The unused medium moved to the supply flow path 22C in the third culture apparatus 20C through the distribution flow path 30 arrives at the first culture vessel 21CA. The unused medium pushes used medium in the first culture vessel 21CA to move it to the discharge vessel 50 through the discharge flow path 26C. This allows the replacement of medium in the first culture vessel 21CA.

The length of the distribution flow path 30 and/or the supply flow path 22 may be set so that the medium arrives at the first culture vessels 21AA, 21BA, and 21CA in the first to third culture apparatuses 20A, 20B, and 20C at the same time. For example, the length of the distribution flow path 30 and/or the supply flow path 22 may be set so that the flow paths from the first fluid storage 11A to each of the first culture vessels 21AA, 21BA, and 21CA have the same length. It should be noted that the first supply valves 24AA, 24BA, and 24CA may be opened at different times to cause arrival of the medium at the first culture vessels 21AA, 21BA, and 21CA in the first to third culture apparatuses 20A, 20B, and 20C at different times.

Before the unused medium is transferred to the first culture vessels 21AA, 21BA, and 21CA, some or all of the medium in each of the first culture vessels 21AA, 21BA, and 21CA may be discharged.

In this case, the controller 301 opens the confluence valve 34D, closes the other confluence valves 33, 34A, 34B, and 34C, and controls the fluid machinery 31 to move the gas in the fourth fluid storage 11D toward the first to third culture apparatuses 20A, 20B, and 20C through the confluence flow path 32 and the distribution flow path 30.

The gas moved from the distribution flow path 30 to the supply flow path 22A in the first culture apparatus 20A arrives at the first culture vessel 21AA. The gas pushes some or all of used medium in the first culture vessel 21AA to move it to the discharge vessel 50 through the discharge flow path 26A. This allows the discharge of some or all of the medium in the first culture vessel 21AA.

The gas moved from the distribution flow path 30 to the supply flow path 22B in the second culture apparatus 20B arrives at the first culture vessel 21BA. The gas pushes some or all of the used medium in the first culture vessel 21BA to move it to the discharge vessel 50 through the discharge flow path 26B. This allows the discharge of some or all of the medium in the first culture vessel 21BA.

The gas moved from the distribution flow path 30 to the supply flow path 22C in the third culture apparatus 20C arrives at the first culture vessel 21CA. The gas pushes some or all of the used medium in the first culture vessel 21CA to move it to the discharge vessel 50 through the discharge flow path 26C. This allows the discharge of some or all of the medium in the first culture vessel 21CA.

Once the media have been replaced in the first culture vessels 21AA, 21BA, and 21CA in the first to third culture apparatuses 20A, 20B, and 20C, the controller 301 controls the fluid machinery 31 to stop the movement of fluid. The controller 301 closes the first supply valve 24AA and the first discharge valve 27AA in the first culture apparatus 20A, the first supply valve 24BA and the first discharge valve 27BA in the second culture apparatus 20B, and the first supply valve 24CA and the first discharge valve 27CA in the third culture apparatus 20C. The cells are cultured in each of the first culture vessels 21AA, 21BA, and 21CA in the first to third culture apparatuses 20A, 20B, and 20C over a predetermined period. The culture may be adhesive culture or suspension culture. The culture may be two-dimensional culture or three-dimensional culture.

When the cells in the first culture vessels 21AA, 21BA, and 21CA are passaged, the controller 301 opens the first supply valve 24AA and the first discharge valve 27AA in the first culture apparatus 20A and closes the other supply valves 24AB and 24AC and the other discharge valves 27AB and 27AC. The controller 301 opens the first supply valve 24BA and the first discharge valve 27BA in the second culture apparatus 20B and closes the other supply valves 24BB and 24BC and the other discharge valves 27BB and 27BC. The controller 301 opens the first supply valve 24CA and the first discharge valve 27CA in the third culture apparatus 20C and closes the other supply valves 24CB and 24CC and the other discharge valves 27CB and 27CC. The controller 301 also opens the confluence valve 34B, closes the other confluence valves 33, 34A, 34C, and 34D, and controls the fluid machinery 31 to move the detachment agent in the second fluid storage 11B toward the first to third culture apparatuses 20A, 20B, and 20C through the confluence flow path 32 and the distribution flow path 30.

The detachment agent moved to the supply flow path 22A in the first culture apparatus 20A through the distribution flow path 30 arrives at the first culture vessel 21AA. The detachment agent pushes the used medium in the first culture vessel 21AA to move it to the discharge vessel 50 through the discharge flow path 26A.

The detachment agent moved from the distribution flow path 30 to the supply flow path 22B in the second culture apparatus 20B arrives at the first culture vessel 21BA. The detachment agent pushes the used medium in the first culture vessel 21BA to move the medium to the discharge vessel 50 through the discharge flow path 26B.

The detachment agent moved from the distribution flow path 30 to the supply flow path 22C in the third culture apparatus 20C arrives at the first culture vessel 21CA. The detachment agent pushes the used medium in the first culture vessel 21CA to move the medium to the discharge vessel 50 through the discharge flow path 26C.

The length of the distribution flow path 30 and/or the supply flow path 22 may be set so that the detachment agent arrives at the first culture vessels 21AA, 21BA, and 21CA in the first to third culture apparatuses 20A, 20B, and 20C at the same time. For example, the length of the distribution flow path 30 and/or the supply flow path 22 may be set so that the flow paths from the second fluid storage 11B to each of the first culture vessels 21AA, 21BA, and 21CA have the same length. It should be noted that the first supply valves 24AA, 24BA, and 24CA may be opened at different times to cause arrival of the detachment agent at the first culture vessels 21AA, 21BA, and 21CA in the first to third culture apparatuses 20A, 20B, and 20C at different times.

Before the detachment agent is transferred to the first culture vessels 21AA, 21BA, and 21CA, some or all of the medium in each of the first culture vessels 21AA, 21BA, and 21CA may be discharged using a gas. A way to discharge some or all of the medium in each of the first culture vessels 21AA, 21BA, and 21CA using a gas is as described above.

Once the detachment agent has entered the first culture vessels 21AA, 21BA, and 21CA in the first to third culture apparatuses 20A, 20B, and 20C, the controller 301 controls the fluid machinery 31 to stop the movement of fluid. The detachment agent is allowed to contact with cells over a predetermined period required to detach the cells from each of the first culture vessels 21AA, 21BA, and 21CA. For suspension culture or three-dimensional culture, the detachment agent is not required to be brought in contact with the cells.

After the predetermined period, the controller 301 closes the confluence valves 33, 34A, 34B, and 34C and opens the confluence valve 34D. The controller 301 also controls the fluid machinery 31 to move the gas in the fourth fluid storage 11D toward the first to third culture apparatuses 20A, 20B, and 20C through the confluence flow path 32 and the distribution flow path 30.

The gas moved from the distribution flow path 30 to the supply flow path 22A in the first culture apparatus 20A arrives at the first culture vessel 21AA. The gas pushes the used detachment agent in the first culture vessel 21AA to move it to the discharge vessel 50 through the discharge flow path 26A.

The gas moved from the distribution flow path 30 to the supply flow path 22B in the second culture apparatus 20B arrives at the first culture vessel 21BA. The gas pushes the used detachment agent in the first culture vessel 21BA to move it to the discharge vessel 50 through the discharge flow path 26B.

The gas moved from the distribution flow path 30 to the supply flow path 22C in the third culture apparatus 20C arrives at the first culture vessel 21CA. The gas pushes the used detachment agent in the first culture vessel 21CA to move it to the discharge vessel 50 through the discharge flow path 26C.

The length of the distribution flow path 30 and/or the supply flow path 22 may be set so that the gas arrives at the first culture vessels 21AA, 21BA, and 21CA in the first to third culture apparatuses 20A, 20B, and 20C at the same time. For example, the length of the distribution flow path 30 and/or the supply flow path 22 may be set so that the flow paths from the fourth fluid storage 11D to each of the first culture vessels 21AA, 21BA, and 21CA have the same length. It should be noted that the first supply valves 24AA, 24BA, and 24CA may be opened at different times to cause arrival of the gas at the first culture vessels 21AA, 21BA, and 21CA in the first to third culture apparatuses 20A, 20B, and 20C at different times.

The controller 301 opens the first supply valve 24AA corresponding to the first culture vessel 21AA in the first culture apparatus 20A, closes the first discharge valve 27AA corresponding to the first culture vessel 21AA and the second supply valve 24AB corresponding to the second culture vessel 21AB, opens the second discharge valve 27AB corresponding to the second culture vessel 21AB, and closes the third supply valve 24AC corresponding to the third culture vessel 21AC and the third discharge valve 27AC corresponding to the third culture vessel 21AC. The controller 301 opens the first connection valve 25AA between the first culture vessel 21AA and the second culture vessel 21AB in the first culture apparatus 20A and closes the second connection valve 25AB between the second culture vessel 21AB and the third culture vessel 21AC.

The controller 301 opens the first supply valve 24BA corresponding to the first culture vessel 21BA in the second culture apparatus 20B, closes the first discharge valve 27BA corresponding to the first culture vessel 21BA and the second supply valve 24BB corresponding to the second culture vessel 21BB, opens the second discharge valve 27BB corresponding to the second culture vessel 21BB, and closes the third supply valve 24BC corresponding to the third culture vessel 21BC and the third discharge valve 27BC corresponding to the third culture vessel 21BC. The controller 301 opens the first connection valve 25BA between the first culture vessel 21BA and the second culture vessel 21BB in the second culture apparatus 20B and closes the second connection valve 25BB between the second culture vessel 21BB and the third culture vessel 21BC.

The controller 301 opens the first supply valve 24CA corresponding to the first culture vessel 21CA in the third culture apparatus 20C, closes the first discharge valve 27CA corresponding to the first culture vessel 21CA and the second supply valve 24CB corresponding to the second culture vessel 21CB, opens the second discharge valve 27CB corresponding to the second culture vessel 21CB, and closes the third supply valve 24CC corresponding to the third culture vessel 21CC and the third discharge valve 27CC corresponding to the third culture vessel 21CC. The controller 301 opens the first connection valve 25CA between the first culture vessel 21CA and the second culture vessel 21CB in the third culture apparatus 20C and closes the second connection valve 25CB between the second culture vessel 21CB and the third culture vessel 21CC.

The controller 301 closes the confluence valves 33, 34B, 34C, and 34D and opens the confluence valve 34A corresponding to the first fluid storage 11A that stores the medium. The controller 301 controls the fluid machinery 31 to move the medium in the first fluid storage 11A toward the first to third culture apparatuses 20A, 20B, and 20C through the confluence flow path 32 and the distribution flow path 30.

The medium moved from the distribution flow path 30 to the supply flow path 22A in the first culture apparatus 20A arrives at the first culture vessel 21AA. The cells in the first culture vessel 21AA disperse in the medium. The medium comprising cells is moved to the second culture vessel 21AB through the connection flow path 23A. The medium comprising the cells pushes a fluid in the second culture vessel 21AB, such as a gas, to move it to the discharge vessel 50 through the discharge flow path 26A.

The medium moved from the distribution flow path 30 to the supply flow path 22B in the second culture apparatus 20B arrives at the first culture vessel 21BA. The cells in the first culture vessel 21BA disperse in the medium. The medium comprising the cells is moved into the second culture vessel 21BB through the connection flow path 23B. The medium comprising cells pushes a fluid in the second culture vessel 21BB, such as a gas, to move it to the discharge vessel 50 through the discharge flow path 26B.

The medium moved from the distribution flow path 30 to the supply flow path 22C in the third culture apparatus 20C arrives at the first culture vessel 21CA. The cells in the first culture vessel 21CA disperse in the medium. The medium comprising the cells is moved into the second culture vessel 21CB through the connection flow path 23C. The medium comprising the cells pushes a fluid in the second culture vessel 21CB, such as a gas, to move it to the discharge vessel 50 through the discharge flow path 26C.

The length of the connection flow paths 23A, 23B, and 23C may be set so that the medium comprising the cells arrives at the second culture vessels 21AB, 21BB, and 21CB respectively from the first culture vessels 21AA, 21BA, and 21CA at the same time. For example, the length of the connection flow paths 23A, 23B, and 23C may be set so that the flow paths from the first culture vessels 21AA, 21BA, and 21CA respectively to the second culture vessels 21AB, 21BB, and 21CB have the same length. It should be noted that the first supply valves 24AA, 24BA, and 24CA may be opened at different times to cause arrival of the medium at the first culture vessels 21AA, 21BA, and 21CA in the first to third culture apparatuses 20A, 20B, and 20C at different times and to cause arrival of the medium comprising cells at the second culture vessels 21AB, 21BB, and 21CB respectively from the first culture vessels 21AA, 21BA, and 21CA at different times.

Once the fluid comprising the cells has entered the second culture vessels 21AB, 21BB, and 21CB in the first to third culture apparatuses 20A, 20B, and 20C, the controller 301 controls the fluid machinery 31 to stop the movement of fluid. The controller 301 closes the first supply valve 24AA, the first connection valve 25AA, and the second discharge valve 27AB in the first culture apparatus 20A, the first supply valve 24BA, the first connection valves 25BA, and the second discharge valve 27BB in the second culture apparatus 20B, and the first supply valve 24CA, the first connection valves 25CA, and the second discharge valve 27CB in the third culture apparatus 20C. The cells are cultured in each of the second culture vessels 21AB, 21BB, and 21CB in the first to third culture apparatuses 20A, 20B, and 20C over a predetermined period. The culture may be adhesive culture or suspension culture. The culture may be two-dimensional culture or three-dimensional culture.

When the media in the second culture vessels 21AB, 21BB, and 21CB are replaced, the controller 301 opens the second supply valve 24AB and the second discharge valve 27AB in the first culture apparatus 20A and closes the other supply valves 24AA and 24AC and the other discharge valves 27AA and 27AC. The controller 301 opens the second supply valve 24BB and the second discharge valve 27BB in the second culture apparatus 20B and closes the other supply valves 24BA and 24BC and the other discharge valves 27BA and 27BC. The controller 301 opens the second supply valve 24CB and the second discharge valve 27CB in the third culture apparatus 20C and closes the other supply valves 24CA and 24CC and the other discharge valves 27CA and 27CC. The controller 301 also opens the confluence valve 34A, closes the other confluence valves 33, 34B, 34C, and 34D, and controls the fluid machinery 31 to move the unused medium in the first fluid storage 11A toward the first to third culture apparatuses 20A, 20B, and 20C through the confluence flow path 32 and the distribution flow path 30.

The unused medium moved to the supply flow path 22A in the first culture apparatus 20A through the distribution flow path 30 arrives at the second culture vessel 21AB. The unused medium pushes the used medium in the second culture vessel 21AB to move it to move to the discharge vessel 50 through the discharge flow path 26A. This allows the replacement of medium in the second culture vessel 21AB.

The unused medium moved from the distribution flow path 30 to the supply flow path 22B in the second culture apparatus 20B arrives at the second culture vessel 21BB. The unused medium pushes the used medium in the second culture vessel 21BB to move it to the discharge vessel 50 through the discharge flow path 26B. This allows the replacement of medium in the second culture vessel 21BB.

The unused medium moved to the supply flow path 22C in the third culture apparatus 20C through the distribution flow path 30 arrives at the second culture vessel 21CB. The unused medium pushes the used medium in the second culture vessel 21CB to move it to the discharge vessel 50 through the discharge flow path 26C. This allows the replacement of medium in the second culture vessel 21CB.

The length of the distribution flow path 30 and/or the supply flow path 22 may be set so that the medium arrives at the second culture vessels 21AB, 21BB, and 21CB in the first to third culture apparatuses 20A, 20B, and 20C at the same time. For example, the length of the distribution flow path 30 and/or the supply flow path 22 may be set so that the flow paths from the first fluid storage 11A to each of the second culture vessels 21AB, 21BB, and 21CB have the same length. It should be noted that the second supply valves 24AB, 24BB, and 24CB may be opened at different times to cause arrival of the medium at the second culture vessels 21AB, 21BB, and 21CB in the first to third culture apparatuses 20A, 20B, and 20C at different times.

Once the media have been replaced in the second culture vessels 21AB, 21BB, and 21CB in the first to third culture apparatuses 20A, 20B, and 20C, the controller 301 controls the fluid machinery 31 to stop the movement of fluid. The controller 301 closes the second supply valve 24AB and the second discharge valve 27AB in the first culture apparatus 20A, the second supply valve 24BB and the second discharge valve 27BB in the second culture apparatus 20B, and the second supply valve 24CB and the second discharge valve 27CB in the third culture apparatus 20C. The cells are cultured in each of the second culture vessels 21AB, 21BB, and 21CB in the first to third culture apparatuses 20A, 20B, and 20C over a predetermined period. The culture may be adhesive culture or suspension culture. The culture may be two-dimensional culture or three-dimensional culture.

When the cells in the second culture vessels 21AB, 21BB, and 21CB are passaged, the controller 301 opens the second supply valve 24AB and the second discharge valve 27AB in the first culture apparatus 20A and closes the other supply valves 24AA and 24AC and the other discharge valves 27AA and 27AC. The controller 301 opens the second supply valve 24BB and the second discharge valve 27BB in the second culture apparatus 20B and closes the other supply valves 24BA and 24BC and the other discharge valves 27BA and 27BC. The controller 301 opens the second supply valve 24CB and the second discharge valve 27CB in the third culture apparatus 20C and closes the other supply valves 24CA and 24CC and the other discharge valves 27CA and 27CC. The controller 301 also opens the confluence valve 34B, closes the other confluence valves 33, 34A, 34C, and 34D, and controls the fluid machinery 31 to move the detachment agent in the second fluid storage 11B toward the first to third culture apparatuses 20A, 20B, and 20C through the confluence flow path 32 and the distribution flow path 30.

The detachment agent moved to the supply flow path 22A in the first culture apparatus 20A through the distribution flow path 30 arrives at the second culture vessel 21AB. The detachment agent pushes the used medium in the second culture vessel 21AB to move it to the discharge vessel 50 through the discharge flow path 26A.

The detachment agent moved from the distribution flow path 30 to the supply flow path 22B in the second culture apparatus 20B arrives at the second culture vessel 21BB. The detachment agent pushes the used medium in the second culture vessel 21BB to move it to the discharge vessel 50 through the discharge flow path 26B.

The detachment agent moved from the distribution flow path 30 to the supply flow path 22C in the third culture apparatus 20C arrives at the second culture vessel 21CB. The detachment agent pushes the used medium in the second culture vessel 21CB to move it to the discharge vessel 50 through the discharge flow path 26C.

The length of the distribution flow path 30 and/or the supply flow path 22 may be set so that the detachment agent arrives at the second culture vessels 21AB, 21BB, and 21CB in the first to third culture apparatuses 20A, 20B, and 20C at the same time. For example, the length of the distribution flow path 30 and/or the supply flow path 22 may be set so that the flow paths from the second fluid storage 11B to each of the second culture vessels 21AB, 21BB, and 21CB have the same length. It should be noted that the second supply valves 24AB, 24BB, and 24CB may be opened at different times to cause arrival of the detachment agent at the second culture vessels 21AB, 21BB, and 21CB in the first to third culture apparatuses 20A, 20B, and 20C at different times.

Once the detachment agent has entered the second culture vessels 21AB, 21BB, and 21CB in the first to third culture apparatuses 20A, 20B, and 20C, the controller 301 controls the fluid machinery 31 to stop the movement of fluid. The detachment agent is allowed to contact with cells over a predetermined period required to detach the cells from each of the second culture vessels 21AB, 21BB, and 21CB. For suspension culture or three-dimensional culture, the detachment agent is not required to be brought in contact with the cells.

After the predetermined period, the controller 301 closes the confluence valves 33, 34A, 34B, and 34C and opens the confluence valve 34D. The controller 301 also controls the fluid machinery 31 to move the gas in the fourth fluid storage 11D toward the first to third culture apparatuses 20A, 20B, and 20C through the confluence flow path 32 and the distribution flow path 30.

The gas moved from the distribution flow path 30 to the supply flow path 22A in the first culture apparatus 20A arrives at the second culture vessel 21AB. The gas pushes the used detachment agent in the second culture vessel 21AB to move it to the discharge vessel 50 through the discharge flow path 26A.

The gas moved from the distribution flow path 30 to the supply flow path 22B in the second culture apparatus 20B arrives at the second culture vessel 21BB. The gas pushes the used detachment agent in the second culture vessel 21BB to move it to the discharge vessel 50 through the discharge flow path 26B.

The gas moved from the distribution flow path 30 to the supply flow path 22C in the third culture apparatus 20C arrives at the second culture vessel 21CB. The gas pushes the used detachment agent in the second culture vessel 21CB to move it to the discharge vessel 50 through the discharge flow path 26C.

The length of the distribution flow path 30 and/or the supply flow path 22 may be set so that the gas arrives at the second culture vessels 21AB, 21BB, and 21CB in the first to third culture apparatuses 20A, 20B, and 20C at the same time. For example, the length of the distribution flow path 30 and/or the supply flow path 22 may be set so that the flow paths from the fourth fluid storage 11D to each of the second culture vessels 21AB, 21BB, and 21CB have the same length. It should be noted that the second supply valves 24AB, 24BB, and 24CB may be opened at different times to cause arrival of the gas at the second culture vessels 21AB, 21BB, and 21CB in the first to third culture apparatuses 20A, 20B, and 20C at different times.

The controller 301 closes the first supply valve 24AA and the first discharge valve 27AA, opens the second supply valve 24AB, closes the second discharge valve 27AB and the third supply valve 24AC, and opens the third discharge valve 27AC in the first culture apparatus 20A. The controller 301 closes the first connection valve 25AA and opens the second connection valve 25AB in the first culture apparatus 20A. The controller 301 closes the harvesting valve 28A provided in the cell harvesting flow path 40A connected to the third culture vessel 21AC.

The controller 301 closes the first supply valve 24BA and the first discharge valve 27BA, opens the second supply valve 24BB, closes the second discharge valve 27BB and the third supply valve 24BC, and opens the third discharge valve 27BC in the second culture apparatus 20B. The controller 301 closes the first connection valve 25BA and opens the second connection valve 25BB in the second culture apparatus 20B. The controller 301 closes the harvesting valve 28B provided in the cell harvesting flow path 40B connected to the third culture vessel 21BC.

The controller 301 closes the first supply valve 24CA and the first discharge valve 27CA, opens the second supply valve 24CB, closes the second discharge valve 27CB and the third supply valve 24CC, and opens the third discharge valve 27CC in the third culture apparatus 20C. The controller 301 closes the first connection valve 25CA and opens the second connection valve 25CB in the third culture apparatus 20C. The controller 301 closes the harvesting valve 28C provided in the cell harvesting flow path 40C connected to the third culture vessel 21CC.

The controller 301 closes the confluence valves 33, 34B, 34C, and 34D and opens the confluence valve 34A corresponding to the first fluid storage 11A that stores a medium. The controller 301 controls the fluid machinery 31 to move the medium in the first fluid storage 11A toward the first to third culture apparatuses 20A, 20B, and 20C through the confluence flow path 32 and the distribution flow path 30.

The medium moved from the distribution flow path 30 to the supply flow path 22A in the first culture apparatus 20A arrives at the second culture vessel 21AB. The cells in the second culture vessel 21AB disperse in the medium. The medium comprising cells is moved into the third culture vessel 21AC through the connection flow path 23A. The medium comprising the cells pushes a fluid in the third culture vessel 21AC, such as a gas, to move it to the discharge vessel 50 through the discharge flow path 26A.

The medium moved from the distribution flow path 30 to the supply flow path 22B in the second culture apparatus 20B arrives at the second culture vessel 21BB. The cells in the second culture vessel 21BB disperse in the medium. The medium comprising cells is moved into the third culture vessel 21BC through the connection flow path 23B. The medium comprising the cells pushes a fluid in the third culture vessel 21BC, such as a gas, to move it to the discharge vessel 50 through the discharge flow path 26B.

The medium moved from the distribution flow path 30 to the supply flow path 22C in the third culture apparatus 20C arrives at the second culture vessel 21CB. The cells in the second culture vessel 21CB disperse in the medium. The medium comprising the cells is moved into the third culture vessel 21CC through the connection flow path 23C. The medium comprising the cells pushes a fluid in the third culture vessel 21CC, such as a gas, to move it to the discharge vessel 50 through the discharge flow path 26C.

The length of the connection flow paths 23A, 23B, and 23C may be set so that the medium comprising the cells arrives at the third culture vessels 21AC, 21BC, and 21CC respectively from the second culture vessels 21AB, 21BB, and 21CB at the same time. For example, the length of the connection flow paths 23A, 23B, and 23C may be set so that the flow paths from the second culture vessels 21AB, 21BB, and 21CB respectively to the third culture vessels 21AC, 21BC, and 21CC have the same length. It should be noted that the first supply valves 24AB, 24BB, and 24CB may be opened at different times to cause arrival of the medium at the second culture vessels 21AB, 21BB, and 21CB in the first to third culture apparatuses 20A, 20B, and 20C at different times and to cause arrival of the medium comprising cells at the third culture vessels 21AC, 21BC, and 21CC respectively from the second culture vessels 21AB, 21BB, and 21CB at different times.

Once the fluid comprising the cells has entered the third culture vessels 21AC, 21BC, and 21CC in the first to third culture apparatuses 20A, 20B, and 20C, the controller 301 controls the fluid machinery 31 to stop the movement of fluid. The controller 301 closes the second supply valve 24AB, the second connection valves 25AB, and the third discharge valve 27AC in the first culture apparatus 20A, the second supply valve 24BB, the second connection valves 25BB, and the third discharge valve 27BC in the second culture apparatus 20B, and the second supply valve 24CB, the second connection valves 25CB, and the third discharge valve 27CC in the third culture apparatus 20C. The cells are cultured in each of the third culture vessels 21AC, 21BC, and 21CC in the first to third culture apparatuses 20A, 20B, and 20C over a predetermined period. The culture may be adhesive culture or suspension culture. The culture may be two-dimensional culture or three-dimensional culture.

When the media in the third culture vessels 21AC, 21BC, and 21CC are replaced, the controller 301 opens the third supply valve 24AC and the third discharge valve 27AC in the first culture apparatus 20A and closes the other supply valves 24AA and 24AB and the other discharge valves 27AA and 27AB. The controller 301 opens the third supply valve 24BC and the third discharge valve 27BC in the second culture apparatus 20B and closes the other supply valves 24BA and 24BB and the other discharge valves 27BA and 27BB. The controller 301 opens the third supply valve 24CC and the third discharge valve 27CC in the third culture apparatus 20C and closes the other supply valves 24CA and 24CB and the other discharge valves 27CA and 27CB. The controller also 301 opens the confluence valve 34A, closes the other confluence valves 33, 34B, 34C, and 34D, and controls the fluid machinery 31 to move the unused medium in the first fluid storage 11A toward the first to third culture apparatuses 20A, 20B, and 20C through the confluence flow path 32 and the distribution flow path 30.

The unused medium moved from the distribution flow path 30 to the supply flow path 22A in the first culture apparatus 20A arrives at the third culture vessel 21AC. The unused medium pushes the used medium in the second culture vessel 21AC to move it to the discharge vessel 50 through the discharge flow path 26A. This allows the replacement of medium in the third culture vessel 21AC.

The unused medium moved from the distribution flow path 30 to the supply flow path 22B in the second culture apparatus 20B arrives at the third culture vessel 21BC. The unused medium pushes the used medium in the third culture vessel 21BC to move it to the discharge vessel 50 through the discharge flow path 26B. This allows the replacement of medium in the third culture vessel 21BC.

The unused medium moved from the distribution flow path 30 to the supply flow path 22C in the third culture apparatus 20C arrives at the third culture vessel 21CC. The unused medium pushes the used medium in the third culture vessel 21CC to move it to the discharge vessel 50 through the discharge flow path 26C. This allows the replacement of medium in the third culture vessel 21CC.

The length of the distribution flow path 30 and/or the supply flow path 22 may be set so that the medium arrives at the third culture vessels 21AC, 21BC, and 21CC in the first to third culture apparatuses 20A, 20B, and 20C at the same time. For example, the length of the distribution flow path 30 and/or the supply flow path 22 may be set so that the flow paths from the first fluid storage 11A to each of the third culture vessels 21AC, 21BC, and 21CC have the same length. It should be noted that the third supply valves 24AC, 24BC, and 24CC may be opened at different times to cause arrival of the medium at the third culture vessels 21AC, 21BC, and 21CC in the first to third culture apparatuses 20A, 20B, and 20C at different times.

Once the media have been replaced in the third culture vessels 21AC, 21BC, and 21CC in the first to third culture apparatuses 20A, 20B, and 20C, the controller 301 controls the fluid machinery 31 to stop the movement of fluid. The controller 301 closes the third supply valve 24AC and the third discharge valve 27AC in the first culture apparatus 20A, the third supply valve 24BC and the third discharge valve 27BC in the second culture apparatus 20B, and the third supply valve 24CC and the third discharge valve 27CC in the third culture apparatus 20C. The cells are cultured in each of the third culture vessels 21AC, 21BC, and 21CC in the first to third culture apparatuses 20A, 20B, and 20C over a predetermined period. The culture may be adhesive culture or suspension culture. The culture may be two-dimensional culture or three-dimensional culture.

When the cells in the third culture vessels 21AC, 21BC, and 21CC are harvested, the controller 301 opens the third supply valve 24AC and the third discharge valve 27AC in the first culture apparatus 20A and closes the other supply valves 24AA and 24AB and the other discharge valves 27AA and 27AB. The controller 301 opens the third supply valve 24BC and the third discharge valve 27BC in the second culture apparatus 20B and closes the other supply valves 24BA and 24BB and the other discharge valves 27BA and 27BB. The controller 301 opens the third supply valve 24CC and the third discharge valve 27CC in the third culture apparatus 20C and closes the other supply valves 24CA and 24CB and the other discharge valves 27CA and 27CB. The controller 301 also opens the confluence valve 34B, closes the other confluence valves 33, 34A, 34C, and 34D, and controls the fluid machinery 31 to move the detachment agent in the second fluid storage 11B toward the first to third culture apparatuses 20A, 20B, and 20C through the confluence flow path 32 and the distribution flow path 30.

The detachment agent moved from the distribution flow path 30 to the supply flow path 22A in the first culture apparatus 20A arrives at the third culture vessel 21AC. The detachment agent pushes the used medium in the third culture vessel 21AC to move it to the discharge vessel 50 through the discharge flow path 26A.

The detachment agent moved from the distribution flow path 30 to the supply flow path 22B in the second culture apparatus 20B arrives at the third culture vessel 21BC. The detachment agent pushes the used medium in the third culture vessel 21BC to move it to the discharge vessel 50 through the discharge flow path 26B.

The detachment agent moved from the distribution flow path 30 to the supply flow path 22C in the third culture apparatus 20C arrives at the third culture vessel 21CC. The detachment agent pushes the used medium in the third culture vessel 21CC to move it to the discharge vessel 50 through the discharge flow path 26C.

The length of the distribution flow path 30 and/or the supply flow path 22 may be set so that the detachment agent arrives at the third culture vessels 21AC, 21BC, and 21CC in the first to third culture apparatuses 20A, 20B, and 20C at the same time. For example, the length of the distribution flow path 30 and/or the supply flow path 22 may be set so that the flow paths from the second fluid storage 11B to each of the third culture vessels 21AC, 21BC, and 21CC have the same length. It should be noted that the third supply valves 24AC, 24BC, and 24CC may be opened at different times to cause arrival of the detachment agent at the third culture vessels 21AC, 21BC, and 21CC in the first to third culture apparatuses 20A, 20B, and 20C at different times.

Once the detachment agent has entered the third culture vessels 21AC, 21BC, and 21CC in the first to third culture apparatuses 20A, 20B, and 20C, the controller 301 controls the fluid machinery 31 to stop the movement of fluid. The detachment agent is allowed to contact with cells over a predetermined period required to detach the cells from each of the third culture vessels 21AC, 21BC, and 21CC. For suspension culture or three-dimensional culture, the detachment agent is not required to be brought in contact with the cells.

After the predetermined period, the controller 301 closes the confluence valves 33, 34A, 34B, and 34C and opens the confluence valve 34D. The controller 301 also controls the fluid machinery 31 to move the gas in the fourth fluid storage 11D toward the first to third culture apparatuses 20A, 20B, and 20C through the confluence flow path 32 and the distribution flow path 30.

The gas moved from the distribution flow path 30 to the supply flow path 22A in the first culture apparatus 20A arrives at the third culture vessel 21AC. The gas pushes the used detachment agent in the third culture vessel 21AC to move it to the discharge vessel 50 through the discharge flow path 26A.

The gas moved from the distribution flow path 30 to the supply flow path 22B in the second culture apparatus 20B arrives at the third culture vessel 21BC. The gas pushes the used detachment agent in the third culture vessel 21BC to move it to the discharge vessel 50 through the discharge flow path 26B.

The gas moved from the distribution flow path 30 to the supply flow path 22C in the third culture apparatus 20C arrives at the third culture vessel 21CC. The gas pushes the used detachment agent in the third culture vessel 21CC to move it to the discharge vessel 50 through the discharge flow path 26C.

The length of the distribution flow path 30 and/or the supply flow path 22 may be set so that the gas arrives at the third culture vessels 21AC, 21BC, and 21CC in the first to third culture apparatuses 20A, 20B, and 20C at the same time. For example, the length of the distribution flow path 30 and/or the supply flow path 22 may be set so that the flow paths from the fourth fluid storage 11D to each of the third culture vessels 21AC, 21BC, and 21CC have the same length. It should be noted that the third supply valves 24AC, 24BC, and 24CC may be opened at different times to cause arrival of the gas at the third culture vessels 21AC, 21BC, and 21CC in the first to third culture apparatuses 20A, 20B, and 20C at different times.

The controller 301 closes the first supply valve 24AA, the first discharge valve 27AA, the second supply valve 24AB, and the second discharge valve 27AB, opens the third supply valve 24AC, and closes the third discharge valve 27AC in the first culture apparatus 20A. The controller 301 closes the first connection valve 25AA and the second connection valve 25AB in the first culture apparatus 20A. The controller 301 opens the harvesting valve 28A.

The controller 301 closes the first supply valve 24BA, the first discharge valve 27BA, the second supply valve 24BB, and the second discharge valve 27BB, opens the third supply valve 24BC, and closes the third discharge valve 27BC in the second culture apparatus 20B. The controller 301 closes the first connection valve 25BA and the second connection valve 25BB in the second culture apparatus 20B. The controller 301 opens the harvesting valve 28B.

The controller 301 closes the first supply valve 24CA, the first discharge valve 27CA, the second supply valve 24CB, and the second discharge valve 27CB, opens the third supply valve 24CC, and closes the third discharge valve 27CC in the third culture apparatus 20C. The controller 301 closes the first connection valve 25CA and the second connection valve 25CB in the third culture apparatus 20C. The controller 301 opens the harvesting valve 28C.

The controller 301 closes the confluence valves 33, 34A, 34B, and 34D and opens the confluence valve 34C corresponding to the third fluid storage 11C that stores the cryopreservation agent. The controller 301 controls the fluid machinery 31 to move the cryopreservation agent in the third fluid storage 11C toward the first to third culture apparatuses 20A, 20B, and 20C through the confluence flow path 32 and the distribution flow path 30.

The cryopreservation agent moved from the distribution flow path 30 to the supply flow path 22A in the first culture apparatus 20A arrives at the third culture vessel 21AC. The cells in the third culture vessel 21AC disperse in the cryopreservation agent. The cryopreservation agent comprising the cells is moved into the cell harvesting vessel 41A through the cell harvesting flow path 40A.

The cryopreservation agent moved from the distribution flow path 30 to the supply flow path 22B in the second culture apparatus 20B arrives at the third culture vessel 21BC. The cells in the third culture vessel 21BC disperse in the cryopreservation agent. The cryopreservation agent comprising the cells is moved into the cell harvesting vessel 41B through the cell harvesting flow path 40B.

The cryopreservation agent moved from the distribution flow path 30 to the supply flow path 22C in the third culture apparatus 20C arrives at the third culture vessel 21CC. The cells in the third culture vessel 21CC disperse in the cryopreservation agent. The cryopreservation agent comprising the cells is moved into the cell harvesting vessel 41C through the cell harvesting flow path 40C.

The length of the distribution flow path 30 and/or the supply flow path 22 may be set so that the cryopreservation agent arrives at the third culture vessels 21AC, 21BC, and 21CC in the first to third culture apparatuses 20A, 20B, and 20C at the same time. For example, the length of the distribution flow path 30 and/or the supply flow path 22 may be set so that the flow paths from the third fluid storage 11C to each of the third culture vessels 21AC, 21BC, and 21CC have the same length. It should be noted that the third supply valves 24AC, 24BC, and 24CC may be opened at different times to cause arrival of the cryopreservation agent at the third culture vessels 21AC, 21BC, and 21CC in the first to third culture apparatuses 20A, 20B, and 20C at different times.

Once the fluid comprising the cells has entered the cell harvesting vessels 41A, 41B, and 41C, the controller 301 controls the fluid machinery 31 to stop the movement of fluid. The controller 301 closes the harvesting valves 28A, 28B, and 28C. Subsequently, the cell harvesting vessels 41A, 41B, and 41C may be removed from the cell harvesting flow paths 40A, 40B, and 40C and then cryopreserved.

It should be noted that any fluids that are not a cryopreservation agent, such as a medium or buffer, may be used when cells are stored in the cell harvesting vessels 41A, 41B, and 41C.

Second Embodiment

Figure 3:
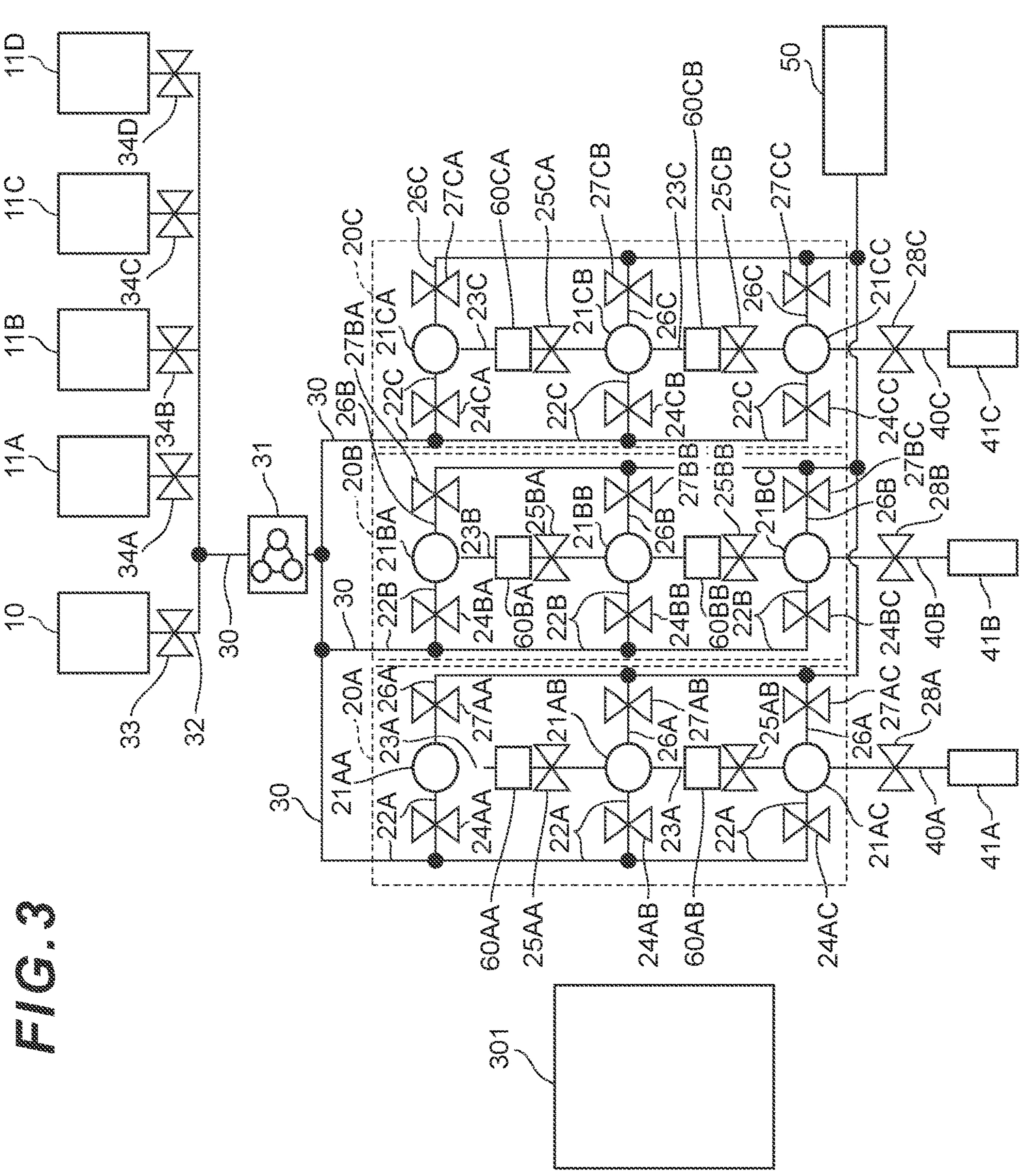
FIG. 3 is a schematic diagram of a culturing system according to the second embodiment.

In a culturing system according to the second embodiment, each of the culture apparatuses 20A, 20B, and 20C further comprises the intermediate tanks 60 provided in the connection flow path 23, as shown in FIG. 3. The intermediate tank 60 is provided between the culture vessels 21. The intermediate tank 60 is configured to store cells. The intermediate tank 60 may comprise a stirrer configured to stir a fluid comprising cells. The intermediate tank 60 may comprise a device that is able to dissociate clumps of cells. Other components in the culturing system according to the second embodiment are similar to those in the first embodiment.

In the second embodiment, when cells in the first culture vessels 21AA, 21BA, and 21CA are adherent-cultured, they are detached from the culture vessels in a similar manner to the first embodiment to move them to the second culture vessels 21AB, 21BB, and 21CB. When the cells are non-adherent-cultured, they are not required to be detached from the culture vessels. Subsequently, the controller 301 controls valves in a similar manner to the first embodiment and controls the fluid machinery 31 to move the medium in the first fluid storage 11A toward the first to third culture apparatuses 20A, 20B, and 20C through the confluence flow path 32 and the distribution flow path 30.

The medium moved from the distribution flow path 30 to the supply flow path 22A in the first culture apparatus 20A arrives at the first culture vessel 21AA. The cells in the first culture vessel 21AA disperse in the medium. The medium comprising the cells is moved into the first intermediate tank 60AA through the connection flow path 23A. The medium comprising the cells pushes a fluid in the first intermediate tank 60AA, such as a gas, to move it to the discharge vessel 50 through the connection flow path 23A, the second culture vessel 21AB, and the discharge flow path 26A.

The medium moved from the distribution flow path 30 to the supply flow path 22B in the second culture apparatus 20B arrives at the first culture vessel 21BA. The cells in the first culture vessel 21BA disperse in the medium. The medium comprising the cells is moved into the first intermediate tank 60BA through the connection flow path 23B. The medium comprising the cells pushes a fluid in the first intermediate tank 60BA, such as a gas, to move it to the discharge vessel 50 through the connection flow path 23B, the second culture vessel 21BB, and the discharge flow path 26B.

The medium moved from the distribution flow path 30 to the supply flow path 22C in the third culture apparatus 20C arrives at the first culture vessel 21CA. The cells in the first culture vessel 21CA disperse in the medium. The medium comprising the cells is moved into the first intermediate tank 60CA through the connection flow path 23C. The medium comprising the cells pushes a fluid in the first intermediate tank 60CA, such as a gas, to move it to the discharge vessel 50 through the connection flow path 23C, the second culture vessel 21CB, and the discharge flow path 26C.

Once the medium comprising cells has entered the first intermediate tanks 60AA, 60BA, and 60CA in the first to third culture apparatuses 20A, 20B, and 20C, the controller 301 controls the fluid machinery 31 to stop the movement of fluid.

For example, once the cells are dispersed homogeneously in the medium in each of the first intermediate tanks 60AA, 60BA, and 60CA, the controller 301 controls the fluid machinery 31 to move the medium in the first fluid storage 11A toward the first to third culture apparatuses 20A, 20B, and 20C through the confluence flow path 32 and the distribution flow path 30.

The medium moved from the distribution flow path 30 to the supply flow path 22A in the first culture apparatus 20A arrives at the first intermediate tank 60AA. The medium comprising the cells in the first intermediate tank 60AA is moved into the second culture vessel 21AB through the connection flow path 23A. The medium comprising the cells pushes a fluid in the second culture vessel 21AB, such as a gas, to move it to the discharge vessel 50 through the discharge flow path 26A.

The medium moved from the distribution flow path 30 to the supply flow path 22B in the second culture apparatus 20B arrives at the first intermediate tank 60BA. The medium comprising the cells in the first intermediate tank 60BA is moved into the second culture vessel 21BB through the connection flow path 23B. The medium comprising the cells pushes a fluid in the second culture vessel 21BB, such as a gas, to move it to the discharge vessel 50 through the discharge flow path 26B.

The medium moved from the distribution flow path 30 to the supply flow path 22C in the third culture apparatus 20C arrives at the first intermediate tank 60CA. The medium comprising the cells in the first intermediate tank 60CA is moved into the second culture vessel 21CB through the connection flow path 23C. The medium comprising the cells pushes a fluid in the second culture vessel 21CB, such as a gas, to move it to the discharge vessel 50 through the discharge flow path 26C.

In the second embodiment, to move cells in the second culture vessels 21AB, 21BB, and 21CB into the third culture vessels 21AC, 21BC, and 21CC, the controller 301 controls valves in a similar manner to the first embodiment and controls the fluid machinery 31 to move the medium in the first fluid storage 11A toward the first to third culture apparatuses 20A, 20B, and 20C through the confluence flow path 32 and the distribution flow path 30.

The medium moved from the distribution flow path 30 to the supply flow path 22A in the first culture apparatus 20A arrives at the second culture vessel 21AB. The cells in the second culture vessel 21AB disperse in the medium. The medium comprising the cells is moved into the second intermediate tank 60AB through the connection flow path 23A. The medium comprising the cells pushes a fluid in the second intermediate tank 60AB, such as a gas, to move it to the discharge vessel 50 through the connection flow path 23A, the third culture vessel 21AC, and the discharge flow path 26A.

The medium moved from the distribution flow path 30 to the supply flow path 22B in the second culture apparatus 20B arrives at the second culture vessel 21BB. The cells in the second culture vessel 21BB disperse in the medium. The medium comprising the cells is moved into the second intermediate tank 60BB through the connection flow path 23B. The medium comprising the cells pushes a fluid in the second intermediate tank 60BB, such as a gas, to move it to the discharge vessel 50 through the connection flow path 23B, the third culture vessel 21BC, and the discharge flow path 26B.

The medium moved from the distribution flow path 30 to the supply flow path 22C in the third culture apparatus 20C arrives at the second culture vessel 21CB. The cells in the second culture vessel 21CB disperse in the medium. The medium comprising the cells is moved into the second intermediate tank 60CB through the connection flow path 23C. The medium comprising the cells pushes a fluid in the second intermediate tank 60CB, such as a gas, to move it to the discharge vessel 50 through the connection flow path 23C, the third culture vessel 21CC, and the discharge flow path 26C.

Once the medium comprising the cells has entered the second intermediate tanks 60AB, 60BB, and 60CB in the first to third culture apparatuses 20A, 20B, and 20C, the controller 301 controls the fluid machinery 31 to stop the movement of fluid.

For example, once the cells are dispersed homogeneously in the medium in each of the second intermediate tanks 60AB, 60BB, and 60CB, the controller 301 controls the fluid machinery 31 to move the medium in the first fluid storage 11A toward the first to third culture apparatuses 20A, 20B, and 20C through the confluence flow path 32 and the distribution flow path 30.

The medium moved from the distribution flow path 30 to the supply flow path 22A in the first culture apparatus 20A arrives at the second intermediate tank 60AB. The medium comprising the cells in the second intermediate tank 60AB is moved into the third culture vessel 21AC through the connection flow path 23A. The medium comprising the cells pushes a fluid in the third culture vessel 21AC, such as a gas, to move it to the discharge vessel 50 through the discharge flow path 26A.

The medium moved from the distribution flow path 30 to the supply flow path 22B in the second culture apparatus 20B arrives at the second intermediate tank 60BB. The medium comprising the cells in the second intermediate tank 60BB is moved into the third culture vessel 21BC through the connection flow path 23B. The medium comprising the cells pushes a fluid in the third culture vessel 21BC, such as a gas, to move it to the discharge vessel 50 through the discharge flow path 26B.

The medium moved from the distribution flow path 30 to the supply flow path 22C in the third culture apparatus 20C arrives at the second intermediate tank 60CB. The medium comprising the cells in the second intermediate tank 60CB is moved into the third culture vessel 21CC through the connection flow path 23C. The medium comprising the cells pushes a fluid in the third culture vessel 21CC, such as a gas, to move it to the discharge vessel 50 through the discharge flow path 26C.

Third Embodiment

Figure 4:
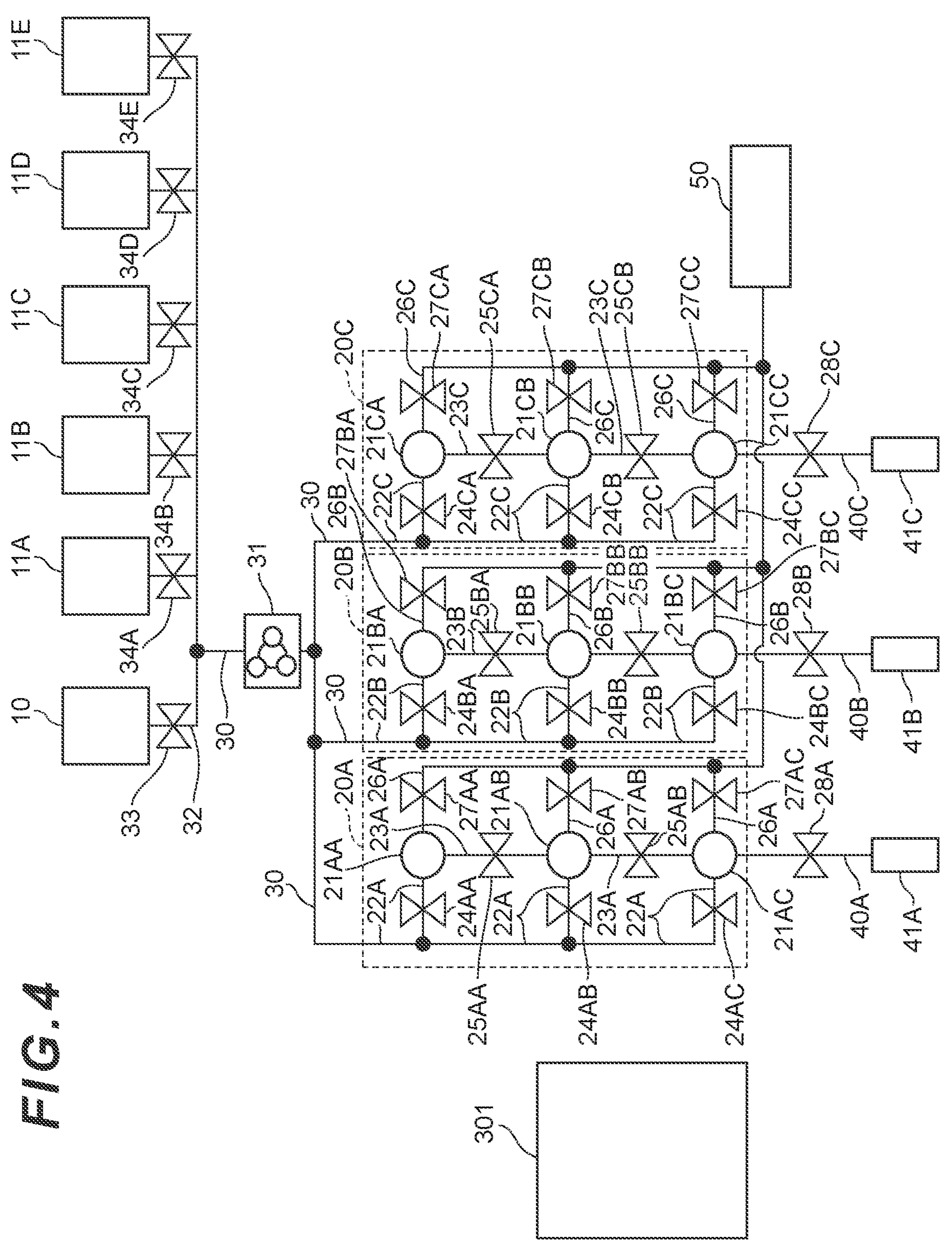
FIG. 4 is a schematic diagram of a culturing system according to the third embodiment.

A culturing system according to the third embodiment may further comprise the fifth fluid storage 11E as shown in FIG. 4. For example, the fifth fluid storage 11E stores factors. For example, the fifth fluid storage 11E has a variable volume. For example, the fifth fluid storage 11E is connected to the confluence flow path 32. The fifth fluid storage 11E may be aseptically connected to the confluence flow path 32. The confluence flow path 32 has the confluence valve 34E corresponding to the fifth fluid storage 11E.

When factors are transferred from the fifth fluid storage 11E to the distribution flow path 30 through the confluence flow path 32, the confluence valve 34E corresponding to the fifth fluid storage 11E is opened, and the other confluence valves 33, 34A, 34B, 34C, and 34D are closed. Other components of the culturing system according to the third embodiment are similar to those in the first embodiment.

The factors are, for example, those that are used to induce cells from a first state to a second state different from the first state. The factors may be a nucleic acid such as a DNA, RNA, or oligonucleotide, a protein, a compound, or a virus. The DNA may be a plasmid DNA. The RNA may be mRNA, siRNA, or miRNA. The RNA may be a modified RNA or an unmodified RNA. The virus may be Sendai virus or lentivirus. In the present disclosure, the term "induction" refers to reprogramming, transformation, transdifferentiation or lineage reprogramming, induction of differentiation, and cell fate reprogramming. A factor that induces cells that are not pluripotent stem cells into pluripotent stem cells is referred to as a reprogramming factor. The reprogramming factor includes, for example, OCT3/4, SOX2, KLF4, and c-MYC. A factor that induces stem cells into differentiated cells is referred to as a differentiation-inducing factor.

Examples of cells in the first state include, but are not limited to, a monocyte, a stem cell, a fibroblast, a neuronal cell, a retinal epithelial cell, a hepatocyte, a β cell, a renal cell, a mesenchymal stem cell, a blood cell, a megakaryocyte, a T cell, a chondrocyte, a cardiomyocyte, a myocyte, a vascular cell, an epithelial cell, a pluripotent stem cell, an ES cell, and an iPS cell.

Examples of cells in the second state include, but are not limited to, a monocyte, a stem cell, a fibroblast, a neuronal cell, a retinal epithelial cell, a hepatocyte, a β cell, a renal cell, a mesenchymal stem cell, a blood cell, a megakaryocyte, a T cell, a chondrocyte, a cardiomyocyte, a myocyte, a vascular cell, an epithelial cell, a pluripotent stem cell, an ES cell, and an iPS cell.

The factors in the fifth fluid storage 11E are distributed to the culture apparatuses 20A, 20B, and 20C by the fluid machinery 31 through the confluence flow path 32 and the distribution flow path 30. For example, the same type and amount of factors are distributed to the culture apparatuses 20A, 20B, and 20C.

Next, a method for transducing factors into cells using the culturing system according to the third embodiment will be described. The method is performed appropriately in combination with the method for culturing cells according to the first embodiment.

In a case where cells are cultured in the first culture vessels 21AA, 21BA, and 21CA and the factors are transferred from the fifth fluid storage 11E to the cells in the first culture vessels 21AA, 21BA, and 21CA, the controller 301 opens the first supply valve 24AA and the first discharge valve 27AA in the first culture apparatus 20A and closes the other supply valves 24AB and 24AC and the other discharge valves 27AB and 27AC. The controller 301 opens the first supply valve 24BA and the first discharge valve 27BA in the second culture apparatus 20B and closes the other supply valves 24BB and 24BC and the other discharge valves 27BB and 27BC. The controller 301 opens the first supply valve 24CA and the first discharge valve 27CA in the third culture apparatus 20C and closes the other supply valves 24CB and 24CC and the other discharge valves 27CB and 27CC. The controller 301 also opens the confluence valve 34E, closes the other confluence valves 33, 34A, 34B, 34C, and 34D, and controls the fluid machinery 31 to move the factors in the fifth fluid storage 11E toward the first to third culture apparatuses 20A, 20B, and 20C through the confluence flow path 32 and the distribution flow path 30.

The factors moved from the distribution flow path 30 to the supply flow path 22A in the first culture apparatus 20A arrive at the first culture vessel 21AA. An excess of fluid in the first culture vessel 21AA is moved to the discharge vessel 50 through the discharge flow path 26A.

The factors moved from the distribution flow path 30 to the supply flow path 22B in the second culture apparatus 20B arrive at the first culture vessel 21BA. An excess of fluid in the first culture vessel 21BA is moved to the discharge vessel 50 through the discharge flow path 26B.

The factors moved from the distribution flow path 30 to the supply flow path 22C in the third culture apparatus 20C arrive at the first culture vessel 21CA. An excess of fluid in the first culture vessel 21CA is moved to the discharge vessel 50 through the discharge flow path 26C.

The length of the distribution flow path 30 and/or the supply flow path 22 may be set so that the factors arrive at the first culture vessels 21AA, 21BA, and 21CA in the first to third culture apparatuses 20A, 20B, and 20C at the same time. For example, the length of the distribution flow path 30 and/or the supply flow path 22 may be set so that the flow paths from the fifth fluid storage 11E to each of the first culture vessels 21AA, 21BA, and 21CA have the same length. It should be noted that the first supply valves 24AA, 24BA, and 24CA may be opened at different times to cause arrival of the factors at the first culture vessels 21AA, 21BA, and 21CA in the first to third culture apparatuses 20A, 20B, and 20C at different times.

Once the factors have entered the first culture vessels 21AA, 21BA, and 21CA in the first to third culture apparatuses 20A, 20B, and 20C, the controller 301 controls the fluid machinery 31 to stop the movement of fluid. The factors are allowed to contact with cells over a predetermined period required to transduce the factors into the cells in each of the first culture vessels 21AA, 21BA, and 21CA. Subsequently, media may be replaced in the first culture vessels 21AA, 21BA, and 21CA as described in the first embodiment.

In a case where the cells are cultured in the second culture vessels 21AB, 21BB, and 21CB and the factors are transferred from the fifth fluid storage 11E to the cells in the second culture vessels 21AB, 21BB, and 21CB, the controller 301 opens the second supply valve 24AB and the second discharge valve 27AB in the first culture apparatus 20A and closes the other supply valves 24AA and 24AC and the other discharge valves 27AA and 27AC. The controller 301 opens the second supply valve 24BB and the second discharge valve 27BB in the second culture apparatus 20B and closes the other supply valves 24BA and 24BC and the other discharge valves 27BA and 27BC. The controller 301 opens the second supply valve 24CB and the second discharge valve 27CB in the third culture apparatus 20C and closes the other supply valves 24CA and 24CC and the other discharge valves 27CA and 27CC. The controller 301 also opens the confluence valve 34E, closes the other confluence valves 33, 34A, 34B, 34C, and 34D, and controls the fluid machinery 31 to move the factors in the fifth fluid storage 11E toward the first to third culture apparatuses 20A, 20B, and 20C through the confluence flow path 32 and the distribution flow path 30.

The factors moved from the distribution flow path 30 to the supply flow path 22A in the first culture apparatus 20A arrive at the second culture vessel 21AB. An excess of fluid in the second culture vessel 21AB is moved to the discharge vessel 50 through the discharge flow path 26A.

The factors moved from the distribution flow path 30 to the supply flow path 22B in the second culture apparatus 20B arrive at the second culture vessel 21BB. An excess of fluid in the second culture vessel 21BB is moved to the discharge vessel 50 through the discharge flow path 26B.

The factors moved from the distribution flow path 30 to the supply flow path 22C in the third culture apparatus 20C arrive at the second culture vessel 21CB. An excess of fluid in the second culture vessel 21CB is moved to the discharge vessel 50 through the discharge flow path 26C.

The length of the distribution flow path 30 and/or the supply flow path 22 may be set so that the factors arrive at the second culture vessels 21AB, 21BB, and 21CB in the first to third culture apparatuses 20A, 20B, and 20C at the same time. For example, the length of the distribution flow path 30 and/or the supply flow path 22 may be set so that the flow paths from the fifth fluid storage 11E to each of the second culture vessels 21AB, 21BB, and 21CB have the same length. It should be noted that the second supply valves 24AB, 24BB, and 24CB may be opened at different times to cause arrival of the factors at the second culture vessels 24AB, 24BB, and 24CB in the first to third culture apparatuses 20A, 20B, and 200 at different times.

Once the factors have entered the second culture vessels 21AB, 21BB, and 21CB in the first to third culture apparatuses 20A, 20B, and 20C, the controller 301 controls the fluid machinery 31 to stop the movement of fluid. The factors are allowed to contact with cells over a predetermined period required to transduce the factors into the cells in each of the second culture vessels 21AB, 21BB, and 21CB. Subsequently, media may be replaced in the second culture vessels 21AB, 21BB, and 21CB as described in the first embodiment.

In a case where the cells are cultured in the third culture vessels 21AC, 21BC, and 21CC and the factors are transferred from the fifth fluid storage 11E to the cells in the third culture vessels 21AC, 21BC, and 21CC, the controller 301 opens the third supply valve 24AC and the third discharge valve 27AC in the first culture apparatus 20A and closes the other supply valves 24AA and 24AB and the other discharge valves 27AA and 27AB. The controller 301 opens the third supply valve 24BC and the third discharge valve 27BC in the second culture apparatus 20B and closes the other supply valves 24BA and 24BB and the other discharge valves 27BA and 27BB. The controller 301 opens the third supply valve 24CC and the third discharge valve 27CC in the third culture apparatus 20C and closes the other supply valves 24CA and 24CB and the other discharge valves 27CA and 27CB. The controller 301 also opens the confluence valve 34E, closes the other confluence valves 33, 34A, 34B, 34C, and 34D, and controls the fluid machinery 31 to move the factors in the fifth fluid storage 11E toward the first to third culture apparatuses 20A, 20B, and 20C through the confluence flow path 32 and the distribution flow path 30.

The factors moved from the distribution flow path 30 to the supply flow path 22A in the first culture apparatus 20A arrive at the third culture vessel 21AC. An excess of fluid in the third culture vessel 21AC is moved to the discharge vessel 50 through the discharge flow path 26A.

The factors moved from the distribution flow path 30 to the supply flow path 22B in the second culture apparatus 20B arrive at the third culture vessel 21BC. An excess of fluid in the third culture vessel 21BC is moved to the discharge vessel 50 through the discharge flow path 26B.

The factors moved from the distribution flow path 30 to the supply flow path 22C in the third culture apparatus 20C arrive at the third culture vessel 21CC. An excess of fluid in the third culture vessel 21CC is moved to the discharge vessel 50 through the discharge flow path 26C.

The length of the distribution flow path 30 and/or the supply flow path 22 may be set so that the factors arrive at the third culture vessels 21AC, 21BC, and 21CC in the first to third culture apparatuses 20A, 20B, and 20C at the same time. For example, the length of the distribution flow path 30 and/or the supply flow path 22 may be set so that the flow paths from the fifth fluid storage 11E to each of the third culture vessels 21AC, 21BC, and 21CC have the same length. It should be noted that the third supply valves 24AC, 24BC, and 24CC may be opened at different times to cause arrival of the factors at the third culture vessels 24AC, 24BC, and 24CC in the first to third culture apparatuses 20A, 20B, and 20C at different times.

Once the factors have entered the third culture vessels 21AC, 21BC, and 21CC in the first to third culture apparatuses 20A, 20B, and 20C, the controller 301 controls the fluid machinery 31 to stop the movement of fluid. The factors are allowed to contact with the cells over a predetermined period required to transduce the factors into the cells in each of the third culture vessels 21AC, 21BC, and 21CC. Subsequently, media may be replaced in the third culture vessels 21AC, 21BC, and 21CC as described in the first embodiment.

The transduction of the factors into cells may be performed in any one or more of the first to third culture vessels 21.

Fourth Embodiment

Figure 5:
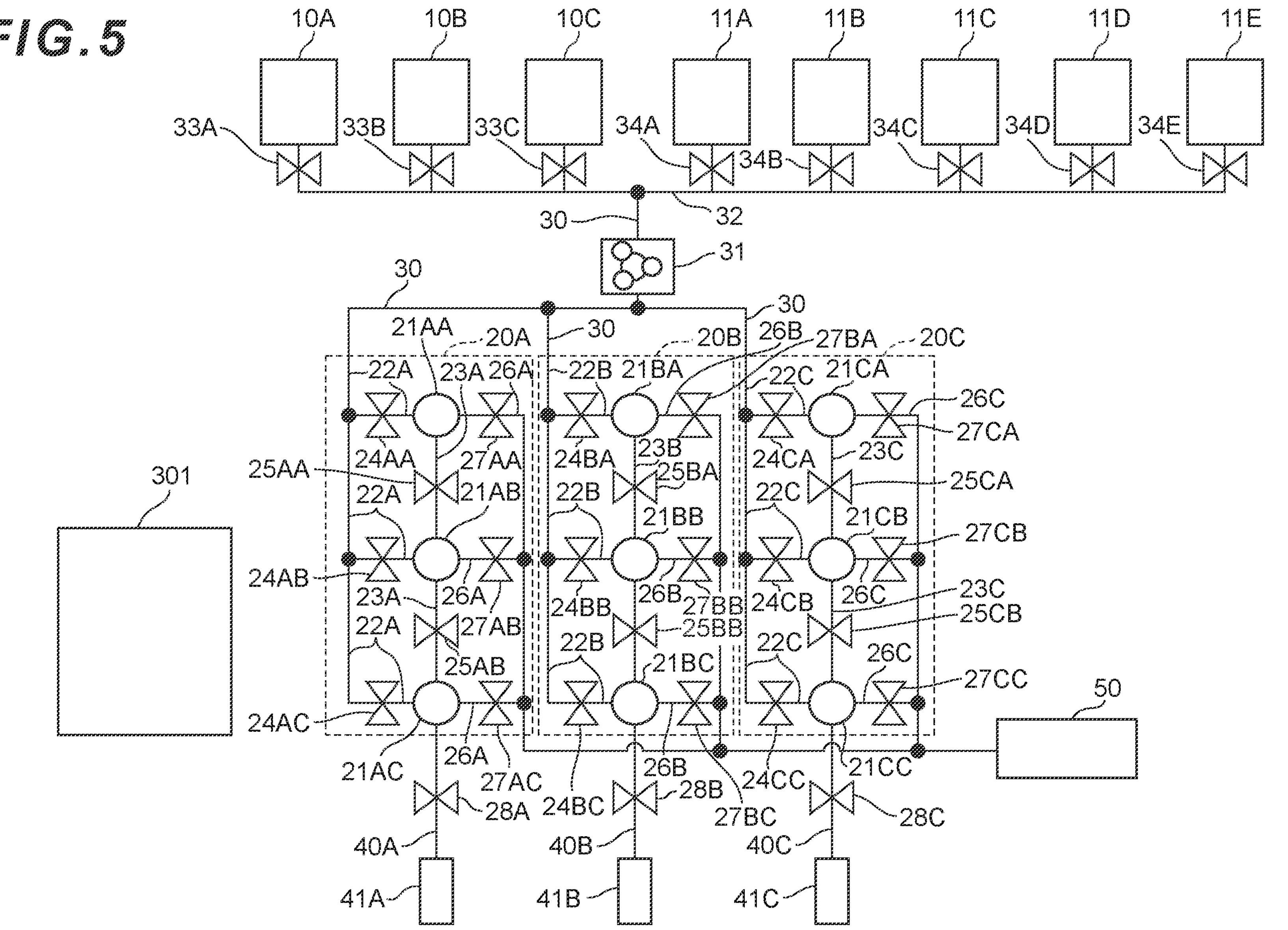
FIG. 5 is a schematic diagram of a culturing system according to the fourth embodiment.

A culturing system according to the fourth embodiment may comprise a plurality of cell storages 10A, 10B, and 10C as shown in FIG. 5. The number of the cell storages is not limited. Cells stored in each of the cell storages 10A, 10B, and 10C are not limited to particular cells. Cells stored in each of the cell storages 10A, 10B, and 10C may be different from one another. The confluence flow path 32 has a plurality of confluence valves 33A, 33B, and 33C respectively corresponding to the cell storages 10A, 10B, and 10C.

When the cells are transferred from the cell storage 10A to the distribution flow path 30 through the confluence flow path 32, the confluence valve 33A corresponding to the cell storage 10A is opened, and the other confluence valves 33B, 33C, 34A, 34B, 34C, and 34D are closed. The cells in the cell storage 10A may be distributed to all of the first to third culture apparatuses 20A to 20C or to at least any of the first to third culture apparatuses 20A to 20C.

When the cells are transferred from the cell storage 10B to the distribution flow path 30 through the confluence flow path 32, the confluence valve 33B corresponding to the cell storage 10B is opened, and the other confluence valves 33A, 33C, 34A, 34B, 34C, and 34D are closed. The cells in the cell storage 10B may be distributed to all of the first to third culture apparatuses 20A to 20C or to at least any of the first to third culture apparatuses 20A to 20C.

When the cells are transferred from the cell storage 10C to the distribution flow path 30 through the confluence flow path 32, the confluence valve 33C corresponding to the cell storage 10C is opened, and the other confluence valves 33A, 33B, 34A, 34B, 34C, and 34D are closed. The cells in the cell storage 10C may be distributed to all of the first to third culture apparatuses 20A to 20C or to at least any of the first to third culture apparatuses 20A to 20C.

Other components of the culturing system according to the fourth embodiment are similar to those in at least any of the culturing systems according to the first to third embodiments.

First Example of Use of a Culturing System According to an Embodiment

Cells are placed in the cell storage 10. Examples of the cells include, but are not limited to, a monocyte, a stem cell, a fibroblast, a neuronal cell, a retinal epithelial cell, a hepatocyte, a β cell, a renal cell, a mesenchymal stem cell, a blood cell, a megakaryocyte, a T cell, a chondrocyte, a cardiomyocyte, a myocyte, a vascular cell, an epithelial cell, a pluripotent stem cell, an ES cell, and an iPS cell.

A density of cells to be placed in the cell storage 10 is set so that a single cell is distributed in each of the culture apparatuses 20. For example, cells are grown from a single cell in the first culture vessel 21 in each of the culture apparatuses 20. In addition, the cells are grown in the second and third culture vessels 21. This results in the establishment of a clone of the cells in each of the culture apparatuses 20.

Second Example of Use of a Culturing System According to an Embodiment

Factors to induce cells from a first state to a second state are transduced into the cells in the first state, and the transduced cells are placed in the cell storage 10. A density of the transduced cells to be placed in the cell storage 10 is set so that a single cell is distributed in each of the culture apparatuses 20. For example, the transduced cells are induced from the first state to the second state in the first culture vessel 21 in each of the culture apparatuses 20, and the cells in the second state are expanded in the second and third culture vessels 21. This results in the establishment of a clone of the induced cells in each of the culture apparatuses 20.

Third Example of Use of a Culturing System According to an Embodiment

Cells are subjected to gene editing and then placed in the cell storage 10. For example, cells may be subjected to gene editing by transducing a protein into the cells. The protein may be a nuclease protein such as a Cas9 protein. A density of the gene-edited cells to be placed in the cell storage 10 is set so that a single cell is distributed in each of the culture apparatuses 20. For example, the cells are grown from a single cell in the first culture vessel 21 in each of the culture apparatuses 20. In addition, the cells are grown in the second and third culture vessels 21. This results in the establishment of a clone of the gene-edited cells in each of the culture apparatuses 20.

Fourth Example of Use of a Culturing System According to an Embodiment

Stem cells are placed in the cell storage 10. Factors to induce stem cells into somatic cells are placed in the fifth fluid storage 11E. A density of the stem cells to be placed in the cell storage 10 is set so that a single cell is distributed in each of the culture apparatuses 20. For example, the stem cells are cultured under suspension culture conditions to form spheroids in the first culture vessel 21 in each of the culture apparatuses 20, and the factors are transduced into the spheroids in the second culture vessel 21. The transduced cells are cultured under adhesive culture conditions to induce somatic cells in the third culture vessel 21. This results in the establishment of the induced somatic cells derived from a single cell in each of the culture apparatuses 20.

Fifth Example of Use of a Culturing System According to an Embodiment

Stem cells are placed in the cell storage 10. Factors to induce stem cells into somatic cells are placed in the fifth fluid storage 11E. A density of the stem cells to be placed in the cell storage 10 is set so that a single cell is distributed in each of the culture apparatuses 20. For example, the stem cells are cultured under adhesive or suspension culture conditions in the first culture vessel 21 in each of the culture apparatuses 20, and the factors are transduced into the stem cells. The induced cells are cultured under adhesive or suspension culture conditions to proliferate in the second and third culture vessels 21. This results in the establishment of the induced somatic cells derived from a single cell in each of the culture apparatuses 20.

Sixth Example of Use of a Culturing System According to an Embodiment

Somatic cells are placed in the cell storage 10. Factors to induce somatic cells into stem cells are placed in the fifth fluid storage 11E. A density of the somatic cells to be placed in the cell storage 10 is set so that a single cell is distributed in each of the culture apparatuses 20. For example, the somatic cells are cultured under adhesive or suspension culture conditions in the first culture vessel 21 in each of the culture apparatuses 20, and the factors are transduced into the somatic cells. The transduced cells are cultured under adhesive or suspension culture conditions to proliferate in the second and third culture vessels 21. This results in the establishment of the induced stem cells derived from a single cell in each of the culture apparatuses 20.

Seventh Example of Use of a Culturing System According to an Embodiment

Differentiation-induced cells are placed in the cell storage 10. Factors to induce the differentiation-induced cells into other differentiated cells are placed in the fifth fluid storage 11E. A density of the differentiation-induced cells to be placed in the cell storage 10 is set so that a single cell is distributed in each of the culture apparatuses 20. For example, the somatic cells are cultured under adhesive or suspension culture conditions, and the factors are transduced into the differentiation-induced cells in the first culture vessel 21 in each of the culture apparatuses 20. The transduced cells are cultured under adhesive or suspension culture conditions to proliferate in the second and third culture vessels 21. This results in lineage specific induction of differentiation in each of the culture apparatuses 20.

Eighth Example of Use of a Culturing System According to an Embodiment

T cells that have been genetically modified to express different chimeric antigen receptors (CARs) (CAR-T cells) are placed in the cell storage 10. A density of the CAR-T cells to be placed in the cell storage 10 is set so that a single cell is distributed in each of the culture apparatuses 20. For example, a first type of single CAR-T cell is distributed into the first culture apparatus 20A, a second type of single CAR-T cell is distributed into the second culture apparatus 20B, and a third type of single CAR-T cell is distributed into the third culture apparatus 20A. For example, cells are grown from a single cell in each of the culture apparatuses 20 in the first culture vessel 21. In addition, cells are grown in the second and third culture vessels 21. This results in the establishment of a clone of the CAR-T cell in each of the culture apparatuses 20.

The present invention has been described in reference to embodiments as mentioned above. However, it should not be understood that the description and drawings which partly form this disclosure limit the present invention. A person skilled in the art would recognize various alternative embodiments, embodiments, and operating techniques in the light of this disclosure. For example, when the supply valve 24AB and the discharge valve 27AB are closed, an atmospheric pressure may prevent fluid in the culture vessel 21AA from entering the connection flow path 23A even with the connection valve 25AA being opened. Therefore, a valve is not required to be closed when a pressure or the like prevents a fluid from passing through the valve in the absence of closing of the valve. Thus, it should be understood that the present invention encompasses various embodiments which are not described herein.

REFERENCE SIGNS LIST

10: cell storage; 11A, 11B, 11C, 11D, 11E: fluid storage; 20, 20A, 20B, 20C: culture apparatus; 21, 21AA, 21AB, 21AC, 21BA, 21BB, 21BC, 21CA, 21CB, 21CC: culture vessel; 22, 22A, 22B, 22C: supply flow path; 23, 23A, 23B, 23C: connection flow path; 24, 24AA, 24AB, 24AC, 24BA, 24BB, 24BC, 24CA, 24CB, 24CC: supply valve; 25, 25AA, 25AB, 25BA, 25BB, 25CA, 25CB: connection valve; 26, 26A, 26B, 26C: discharge flow path; 27, 27AA, 27AB, 27AC, 27BA, 27BB, 27BC, 27CA, 27CB, 27CC: discharge valve; 28, 28A, 28B, 28C: harvesting valve; 30: distribution flow path; 31: fluid machinery; 32: confluence flow path; 33, 34A, 34B, 34C, 34D, 34E: confluence valve; 40, 40A, 40B, 40C: cell harvesting flow path; 41, 41A, 41B, 41C: cell harvesting vessel; 50: discharge vessel; 60, 60AA, 60AB, 60BA, 60BB, 60CA, 60CB: intermediate tank; 301: controller

What is claimed is:

1. A culture system comprising:

a cell storage configured to store cells;

a plurality of culture apparatuses; and a distribution flow path configured to distribute the cells from the cell storage to the plurality of culture apparatuses, wherein each of the plurality of culture apparatuses comprises:

a plurality of culture vessels;

a supply flow path configured to selectively supply a fluid from the distribution flow path to the plurality of culture vessels; and a connection flow path configured to connect the plurality of culture vessels, wherein the plurality of culture vessels is connected in series with the connection flow path in each of the plurality of culture apparatuses, and wherein the supply flow path is configured to selectively supply the fluid to the plurality of culture vessels so that the cells are sequentially transferred among the plurality of culture vessels through the connection flow path in each of the plurality of culture apparatuses, wherein each of the plurality of culture apparatuses further comprises:

a plurality of supply valves provided in the supply flow path;

a discharge flow path configured to selectively discharge a fluid from the plurality of culture vessels; and a plurality of discharge valves provided in the discharge flow path, wherein the plurality of supply valves correspond to the plurality of culture vessels, respectively, in each of the plurality of culture apparatuses, wherein the plurality of discharge valves correspond to the plurality of culture vessels, respectively, in each of the plurality of culture apparatuses, wherein one of the plurality of supply valves corresponding to one of the plurality of culture vessels that is to be provided with the cells from the cell storage is opened, and wherein one of the plurality of discharge valves corresponding to one of the plurality of culture vessels that is to be provided with the cells from the cell storage is opened.

2. The culture system according to claim 1, further comprising one or more fluid storages configured to store a fluid, wherein the distribution flow path is configured to distribute the fluid from the one or more fluid storages to the plurality of culture apparatuses.

3. The culture system according to claim 2, wherein the fluid comprises a medium, a buffer, a cell detachment agent, a cryopreservation agent, or a factor.

4. A culture system comprising:

a cell storage configured to store cells;

a plurality of culture apparatuses; and a distribution flow path configured to distribute the cells from the cell storage to the plurality of culture apparatuses, wherein each of the plurality of culture apparatuses comprises:

a plurality of culture vessels;

a supply flow path configured to selectively supply a fluid from the distribution flow path to the plurality of culture vessels; and a connection flow path configured to connect the plurality of culture vessels, wherein the plurality of culture vessels is connected in series with the connection flow path in each of the plurality of culture apparatuses, and wherein the supply flow path is configured to selectively supply the fluid to the plurality of culture vessels so that the cells are sequentially transferred among the plurality of culture vessels through the connection flow path in each of the plurality of culture apparatuses, wherein each of the plurality of culture apparatuses further comprises:

a plurality of supply valves provided in the supply flow path;

a discharge flow path configured to selectively discharge a fluid from the plurality of culture vessels; and a plurality of discharge valves provided in the discharge flow path, wherein the plurality of supply valves correspond to the plurality of culture vessels, respectively, in each of the plurality of culture apparatuses, wherein the plurality of discharge valves correspond to the plurality of culture vessels, respectively, in each of the plurality of culture apparatuses, wherein one of the plurality of supply valves corresponding to one of the plurality of culture vessels that is to be provided with the fluid is opened, and wherein one of the plurality of discharge valves corresponding to one of the plurality of culture vessels that is to be provided with the fluid is opened.

5. The culture system according to claim 4, further comprising one or more fluid storages configured to store a fluid, wherein the distribution flow path is configured to distribute the fluid from the one or more fluid storages to the plurality of culture apparatuses.

6. The culture system according to claim 5, wherein the fluid comprises a medium, a buffer, a cell detachment agent, a cryopreservation agent, or a factor.

7. A culture system comprising:

a cell storage configured to store cells;

a plurality of culture apparatuses; and a distribution flow path configured to distribute the cells from the cell storage to the plurality of culture apparatuses, wherein each of the plurality of culture apparatuses comprises:

a plurality of culture vessels;

a supply flow path configured to selectively supply a fluid from the distribution flow path to the plurality of culture vessels; and a connection flow path configured to connect the plurality of culture vessels, wherein the plurality of culture vessels is connected in series with the connection flow path in each of the plurality of culture apparatuses, and wherein the supply flow path is configured to selectively supply the fluid to the plurality of culture vessels so that the cells are sequentially transferred among the plurality of culture vessels through the connection flow path in each of the plurality of culture apparatuses, wherein each of the plurality of culture apparatuses further comprises:

a plurality of supply valves provided in the supply flow path;

a plurality of connection valves provided in the connection flow path;

a discharge flow path configured to selectively discharge a fluid from the plurality of culture vessels; and a plurality of discharge valves provided in the discharge flow path, wherein the plurality of supply valves correspond to the plurality of culture vessels, respectively, in each of the plurality of culture apparatuses, wherein the connection valves are provided between the culture vessels in each of the plurality of culture apparatuses, wherein the plurality of discharge valves correspond to the plurality of culture vessels, respectively, in each of the plurality of culture apparatuses, wherein one of the plurality of supply valves corresponding to one of the plurality of culture vessels where the cells are disposed is opened, and wherein the connection valve between the culture vessel where the cells are disposed and a culture vessel adjacent to the culture vessel where the cells are disposed is opened, and wherein one of the plurality of discharge valves corresponding to the adjacent culture vessel is opened.

8. The culture system according to claim 7, further comprising one or more fluid storages configured to store a fluid, wherein the distribution flow path is configured to distribute the fluid from the one or more fluid storages to the plurality of culture apparatuses.

9. The culture system according to claim 8, wherein the fluid comprises a medium, a buffer, a cell detachment agent, a cryopreservation agent, or a factor.

* * * * *